US007744615B2

(12) United States Patent
Couture

(10) Patent No.: US 7,744,615 B2
(45) Date of Patent: Jun. 29, 2010

(54) APPARATUS AND METHOD FOR TRANSECTING TISSUE ON A BIPOLAR VESSEL SEALING INSTRUMENT

(75) Inventor: Gary M. Couture, Longmont, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 472 days.

(21) Appl. No.: 11/488,318

(22) Filed: Jul. 18, 2006

(65) Prior Publication Data
US 2008/0021450 A1  Jan. 24, 2008

(51) Int. Cl.
A61B 17/32 (2006.01)
A61B 18/12 (2006.01)

(52) U.S. Cl. ......................................... 606/171; 606/51

(58) Field of Classification Search ................. 606/108, 606/167, 170–172, 174, 182–183, 185, 205–210, 606/213, 216, 45–46, 49–52
See application file for complete search history.

(56) References Cited

U.S. PATENT DOCUMENTS

| 371,664 | A | 10/1887 | Brannan et al. |
| 702,472 | A | 6/1902 | Pignolet |
| 728,883 | A | 5/1903 | Downes |
| 1,586,645 | A | 6/1926 | Bierman |
| 1,813,902 | A | 7/1931 | Bovie |
| 2,002,594 | A | 5/1935 | Wappler et al. |
| 2,011,169 | A | 8/1935 | Wappler |
| 2,031,682 | A | 2/1936 | Wappler et al. |
| 2,176,479 | A | 10/1939 | Willis |
| 2,279,753 | A | 4/1942 | Knopp |
| 2,305,156 | A | 12/1942 | Grubel |
| 2,632,661 | A | 3/1953 | Cristofv |
| 2,668,538 | A | 2/1954 | Baker |
| 2,796,065 | A | 6/1957 | Kapp |
| 3,459,187 | A | 8/1969 | Pallotta |
| 3,643,663 | A | 2/1972 | Sutter |

(Continued)

FOREIGN PATENT DOCUMENTS

CA  2104423  2/1994

(Continued)

OTHER PUBLICATIONS

International Search Report EP 07014016; dated Jan. 28, 2008.

(Continued)

Primary Examiner—Anhtuan T Nguyen
Assistant Examiner—Ashley Cronin

(57) ABSTRACT

An electrosurgical forceps for sealing tissue is adapted to include a pair of movable jaw members that cooperate to grasp tissue. At least one of the jaw members has a blade channel defined therein configured for sliding reception of a surgical blade assembly, the blade channel including a plurality of troughs and a blade body having a plurality of cutting elements extending therealong, each of the cutting elements including a cutting edge extendable into the blade channel and a flange extending into each of the troughs. The blade body is selectively movable from a first position wherein the cutting edges of the cutting elements are spaced relative to the blade channel and the flanges are rest within the troughs to at least one second position wherein the cutting edges extend within the blade channel.

11 Claims, 10 Drawing Sheets

U.S. PATENT DOCUMENTS

| | | | |
|---|---|---|---|
| 3,651,811 A | 3/1972 | Hildebrandt et al. |
| 3,720,896 A | 3/1973 | Beierlein |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,233,734 A | 11/1980 | Bies |
| 4,300,564 A | 11/1981 | Furihata |
| D263,020 S | 2/1982 | Rau, III |
| 4,370,980 A | 2/1983 | Lottick |
| 4,375,218 A | 3/1983 | Digeronimo |
| 4,416,276 A | 11/1983 | Newton et al. |
| 4,418,692 A | 12/1983 | Guay |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | Desatnick |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,846,171 A | 7/1989 | Kauphusman et al. |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,035,695 A | 7/1991 | Weber, Jr. et al. |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Xamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,314,445 A | 5/1994 | Degwitz et al. |
| 5,318,589 A | 6/1994 | Lichtman |
| 5,324,289 A | 6/1994 | Eggers |
| 5,326,806 A | 7/1994 | Yokoshima et al. |
| 5,330,471 A | 7/1994 | Eggers |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,352,222 A | 10/1994 | Rydell |
| 5,354,271 A | 10/1994 | Voda |
| 5,356,408 A | 10/1994 | Rydell |
| 5,366,477 A | 11/1994 | Lemarie, III et al. |
| 5,368,600 A | 11/1994 | Failla et al. |
| 5,376,089 A | 12/1994 | Smith |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |

| | | | | | | |
|---|---|---|---|---|---|---|
| 5,540,715 A | 7/1996 | Katsaros et al. | | 5,810,877 A | 9/1998 | Roth et al. |
| 5,542,945 A | 8/1996 | Fritzsch | | 5,814,043 A | 9/1998 | Shapeton |
| 5,558,671 A | 9/1996 | Yates | | 5,817,083 A | 10/1998 | Williamson, IV et al. |
| 5,558,672 A | 9/1996 | Edwards et al. | | 5,820,630 A | 10/1998 | Lind |
| 5,562,699 A | 10/1996 | Heimberger et al. | | 5,827,271 A | 10/1998 | Buysse et al. |
| 5,569,241 A | 10/1996 | Edwardds | | 5,827,279 A | 10/1998 | Hughett et al. |
| 5,569,243 A | 10/1996 | Kortenbach et al. | | 5,827,281 A | 10/1998 | Levin |
| 5,571,100 A | 11/1996 | Goble et al. | | 5,827,323 A | 10/1998 | Klieman et al. |
| 5,573,424 A | 11/1996 | Poppe | | 5,827,548 A | 10/1998 | Lavallee et al. |
| 5,573,534 A | 11/1996 | Stone | | 5,833,690 A | 11/1998 | Yates et al. |
| 5,573,535 A | 11/1996 | Viklund | | 5,843,080 A | 12/1998 | Fleenor et al. |
| 5,575,805 A | 11/1996 | Li | | 5,849,022 A | 12/1998 | Sakashita et al. |
| 5,578,052 A | 11/1996 | Koros et al. | | 5,853,412 A | 12/1998 | Mayenberger |
| 5,582,611 A | 12/1996 | Tsukagoshi et al. | | 5,860,976 A | 1/1999 | Billings et al. |
| 5,585,896 A | 12/1996 | Yamazaki et al. | | 5,876,401 A | 3/1999 | Schulze et al. |
| 5,590,570 A | 1/1997 | Lemaire, III et al. | | 5,882,567 A | 3/1999 | Cavallaro et al. |
| 5,597,107 A | 1/1997 | Knodel | | 5,891,141 A | 4/1999 | Rydell |
| 5,601,601 A | 2/1997 | Tal et al. | | 5,891,142 A | 4/1999 | Eggers et al. |
| 5,603,711 A | 2/1997 | Parins et al. | | 5,893,863 A | 4/1999 | Yoon |
| 5,603,723 A | 2/1997 | Aranyi et al. | | 5,893,875 A | 4/1999 | O'Connor et al. |
| 5,611,798 A | 3/1997 | Eggers | | 5,893,877 A | 4/1999 | Gampp, Jr. et al. |
| 5,620,453 A | 4/1997 | Nallakrishnan | | 5,902,301 A | 5/1999 | Olig |
| 5,624,452 A | 4/1997 | Yates | | 5,906,630 A | 5/1999 | Anderhub et al. |
| 5,626,578 A | 5/1997 | Tihon | | 5,908,420 A | 6/1999 | Parins et al. |
| 5,626,609 A | 5/1997 | Zvenyatsky et al. | | 5,908,432 A | 6/1999 | Pan |
| 5,630,833 A | 5/1997 | Katsaros et al. | | 5,911,719 A | 6/1999 | Eggers |
| 5,637,110 A | 6/1997 | Pennybacker et al. | | 5,913,874 A | 6/1999 | Berns et al. |
| 5,638,003 A | 6/1997 | Hall | | 5,921,984 A | 7/1999 | Sutcu et al. |
| 5,643,294 A | 7/1997 | Tovey et al. | | 5,925,043 A | 7/1999 | Kumar et al. |
| 5,647,869 A | 7/1997 | Goble et al. | | 5,935,126 A | 8/1999 | Riza |
| 5,647,871 A | 7/1997 | Levine et al. | | 5,944,718 A | 8/1999 | Dafforn et al. |
| 5,649,959 A | 7/1997 | Hannam et al. | | 5,951,549 A | 9/1999 | Richardson et al. |
| 5,658,281 A | 8/1997 | Heard | | 5,954,720 A | 9/1999 | Wilson et al. |
| 5,662,667 A | 9/1997 | Knodel | | 5,957,923 A | 9/1999 | Hahnen et al. |
| 5,665,100 A | 9/1997 | Yoon | | 5,960,544 A | 10/1999 | Beyers |
| 5,667,526 A | 9/1997 | Levin | | 5,961,514 A | 10/1999 | Long et al. |
| 5,674,220 A | 10/1997 | Fox et al. | | 5,964,758 A | 10/1999 | Dresden |
| 5,681,282 A | 10/1997 | Eggers et al. | | 5,976,132 A | 11/1999 | Morris |
| 5,688,270 A | 11/1997 | Yates et al. | | 5,984,939 A | 11/1999 | Yoon |
| 5,693,051 A | 12/1997 | Schulze et al. | | 5,989,277 A | 11/1999 | Lemaire, III et al. |
| 5,695,522 A | 12/1997 | Lemaire, III et al. | | 5,997,565 A | 12/1999 | Inoue |
| 5,700,261 A | 12/1997 | Brinkerhoff | | 6,004,335 A | 12/1999 | Vaitekunas et al. |
| 5,702,390 A | 12/1997 | Austin et al. | | 6,010,516 A | 1/2000 | Hulka et al. |
| 5,707,369 A | 1/1998 | Vaitekunas et al. | | 6,024,741 A | 2/2000 | Williamson et al. |
| 5,709,680 A | 1/1998 | Yates et al. | | 6,024,744 A | 2/2000 | Kese et al. |
| 5,716,366 A | 2/1998 | Yates | | 6,030,384 A | 2/2000 | Nezhat |
| 5,720,744 A | 2/1998 | Eggleston et al. | | 6,033,399 A | 3/2000 | Gines |
| 5,722,421 A | 3/1998 | Francese et al. | | 6,039,733 A | 3/2000 | Buysse et al. |
| 5,725,536 A | 3/1998 | Oberlin et al. | | 6,041,679 A | 3/2000 | Slater et al. |
| 5,727,428 A | 3/1998 | Lemaire, III et al. | | 6,050,996 A | 4/2000 | Schmaltz et al. |
| 5,735,848 A | 4/1998 | Yates et al. | | 6,053,914 A | 4/2000 | Eggers et al. |
| 5,743,906 A | 4/1998 | Parins et al. | | 6,053,933 A | 4/2000 | Balazs et al. |
| 5,755,717 A | 5/1998 | Yates et al. | | D424,694 S | 5/2000 | Tetzlaff et al. |
| 5,766,130 A | 6/1998 | Selmonosky | | D425,201 S | 5/2000 | Tetzlaff et al. |
| 5,766,166 A | 6/1998 | Hooven | | 6,059,782 A | 5/2000 | Novak et al. |
| 5,766,170 A | 6/1998 | Eggers | | 6,074,386 A | 6/2000 | Goble et al. |
| 5,769,849 A | 6/1998 | Eggers | | RE36,795 E | 7/2000 | Rydell |
| 5,772,655 A | 6/1998 | Bauer et al. | | 6,083,223 A | 7/2000 | Baker |
| 5,772,670 A | 6/1998 | Brosa | | 6,086,586 A | 7/2000 | Hooven |
| 5,776,128 A | 7/1998 | Eggers | | 6,090,107 A | 7/2000 | Borgmeier et al. |
| 5,776,130 A | 7/1998 | Buysse et al. | | 6,096,037 A | 8/2000 | Mulier et al. |
| 5,779,701 A | 7/1998 | McBrayer et al. | | 6,099,550 A | 8/2000 | Yoon |
| H1745 H | 8/1998 | Paraschac | | 6,102,909 A | 8/2000 | Chen et al. |
| 5,792,137 A | 8/1998 | Carr et al. | | 6,110,171 A | 8/2000 | Rydell |
| 5,792,177 A | 8/1998 | Kaseda | | 6,113,596 A | 9/2000 | Hooven et al. |
| 5,797,927 A | 8/1998 | Yoon | | 6,113,598 A | 9/2000 | Baker |
| 5,797,938 A | 8/1998 | Paraschac et al. | | 6,117,158 A | 9/2000 | Measamer et al. |
| 5,797,941 A * | 8/1998 | Schulze et al. .............. 606/171 | | 6,123,701 A | 9/2000 | Nezhat |
| 5,797,958 A | 8/1998 | Yoon | | H1904 H | 10/2000 | Yates et al. |
| 5,800,449 A | 9/1998 | Wales | | 6,126,658 A | 10/2000 | Baker |
| 5,807,393 A | 9/1998 | Williamsom, IV et al. | | 6,152,923 A | 11/2000 | Ryan |
| 5,810,808 A | 9/1998 | Eggers | | 6,162,220 A | 12/2000 | Nezhat |
| 5,810,811 A | 9/1998 | Yates et al. | | 6,174,309 B1 | 1/2001 | Wrublewski et al. |

| | | |
|---|---|---|
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,217,602 B1 | 4/2001 | Redmon |
| 6,221,039 B1 | 4/2001 | Durgin et al. |
| 6,224,593 B1 | 5/2001 | Ryan et al. |
| 6,228,080 B1 | 5/2001 | Gines |
| 6,228,083 B1 | 5/2001 | Lands et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,302,424 B1 | 10/2001 | Gisinger et al. |
| 6,319,451 B1 | 11/2001 | Brune |
| 6,322,561 B1 | 11/2001 | Eggers et al. |
| 6,334,860 B1 | 1/2002 | Dorn |
| 6,334,861 B1 | 1/2002 | Chandler et al. |
| 6,345,532 B1 | 2/2002 | Coudray et al. |
| 6,350,264 B1 | 2/2002 | Hooven |
| 6,352,536 B1 | 3/2002 | Buysse et al. |
| 6,358,249 B1 | 3/2002 | Chen et al. |
| 6,358,268 B1 | 3/2002 | Hunt et al. |
| D457,958 S | 5/2002 | Dycus et al. |
| D457,959 S | 5/2002 | Tetzlaff et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,130 B1 | 10/2002 | Frazier et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,500,176 B1 | 12/2002 | Truckai et al. |
| 6,511,480 B1 | 1/2003 | Tetzlaff et al. |
| 6,514,252 B2 | 2/2003 | Nezhat et al. |
| 6,527,771 B1 | 3/2003 | Weadock et al. |
| 6,558,385 B1 | 5/2003 | McClurken et al. |
| 6,562,037 B2 | 5/2003 | Paton et al. |
| 6,585,735 B1 | 7/2003 | Frazier et al. |
| 6,602,252 B2 | 8/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,626,901 B1 | 9/2003 | Treat et al. |
| 6,641,595 B1 | 11/2003 | Moran et al. |
| 6,652,514 B2 | 11/2003 | Ellman et al. |
| 6,652,521 B2 | 11/2003 | Schulze |
| 6,656,177 B2 | 12/2003 | Truckai et al. |
| 6,660,072 B2 | 12/2003 | Chatterjee |
| 6,669,696 B2 | 12/2003 | Bacher et al. |
| 6,676,660 B2 | 1/2004 | Wampler et al. |
| 6,679,882 B1 | 1/2004 | Kornerup |
| 6,682,527 B2 | 1/2004 | Strul |
| 6,682,528 B2 | 1/2004 | Frazier et al. |
| 6,685,724 B1 | 2/2004 | Haluck |
| 6,689,131 B2 | 2/2004 | McClurken |
| 6,692,445 B2 | 2/2004 | Roberts et al. |
| 6,695,840 B2 | 2/2004 | Schulze |
| 6,702,810 B2 | 3/2004 | McClurken et al. |
| 6,726,068 B2 | 4/2004 | Miller |
| 6,726,686 B2 | 4/2004 | Buysse et al. |
| 6,733,498 B2 | 5/2004 | Paton et al. |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,757,977 B2 | 7/2004 | Dambal et al. |
| 6,770,072 B1 | 8/2004 | Truckai et al. |
| 6,773,409 B2 | 8/2004 | Truckai et al. |
| 6,773,434 B2 | 8/2004 | Ciarrocca |
| 6,775,575 B2 | 8/2004 | Bommannan et al. |
| 6,776,780 B2 | 8/2004 | Mulier et al. |
| 6,790,217 B2 | 9/2004 | Schulze et al. |
| 6,796,981 B2 | 9/2004 | Wham et al. |
| D496,997 S | 10/2004 | Dycus et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,860,880 B2 | 3/2005 | Treat et al. |
| 6,887,240 B1 | 5/2005 | Lands et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| 6,942,662 B2 | 9/2005 | Goble et al. |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,977,495 B2 | 12/2005 | Donofrio |
| 6,979,786 B2 | 12/2005 | Aukland et al. |
| 6,994,707 B2 | 2/2006 | Ellman et al. |
| 6,994,709 B2 | 2/2006 | Iida |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,496 B2 | 5/2006 | Yamauchi |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |

| Patent/Pub No. | Date | Inventor |
|---|---|---|
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,314,471 B2 | 1/2008 | Holman |
| 7,329,256 B2 | 2/2008 | Johnson et al. |
| 7,329,257 B2 | 2/2008 | Kanehira et al. |
| D564,662 S | 3/2008 | Moses et al. |
| 7,342,754 B2 | 3/2008 | Fitzgerald et al. |
| 7,344,268 B2 | 3/2008 | Jigamian |
| 7,367,976 B2 | 5/2008 | Lawes et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069571 A1 | 4/2003 | Treat et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158549 A1 | 8/2003 | Swanson |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0162557 A1 | 8/2004 | Tetzlaff et al. |
| 2004/0176762 A1 | 9/2004 | Lawes et al. |
| 2004/0193153 A1 | 9/2004 | Sarter et al. |
| 2004/0225288 A1 | 11/2004 | Buysse et al. |
| 2004/0230189 A1 | 11/2004 | Keppel |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0154387 A1* | 7/2005 | Moses et al. .................. 606/51 |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0064085 A1 | 3/2006 | Schechter et al. |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |

| | | | | | | |
|---|---|---|---|---|---|---|
| 2007/0173811 | A1 | 7/2007 | Couture et al. | EP | 1632192 A1 | 3/2006 |
| 2007/0173814 | A1 | 7/2007 | Hixson et al. | EP | 1645238 A1 | 4/2006 |
| 2007/0179499 | A1 | 8/2007 | Garrison | EP | 1645240 | 4/2006 |
| 2007/0203485 | A1 | 8/2007 | Keppel | EP | 1645240 A2 | 4/2006 |
| 2007/0213706 | A1 | 9/2007 | Dumbauld et al. | EP | 1707143 A1 | 10/2006 |
| 2007/0213707 | A1 | 9/2007 | Dumbauld et al. | GB | 2214430 A | 6/1989 |
| 2007/0213708 | A1 | 9/2007 | Dumbauld et al. | GB | 2213416 | 8/1989 |
| 2007/0213712 | A1 | 9/2007 | Buysse et al. | JP | 501068 | 9/1984 |
| 2007/0255279 | A1 | 11/2007 | Buysse et al. | JP | 502328 | 3/1992 |
| 2007/0260235 | A1 | 11/2007 | Podhajsky | JP | 5-5106 | 1/1993 |
| 2007/0260238 | A1 | 11/2007 | Guerra | JP | 5-40112 | 2/1993 |
| 2007/0260241 | A1 | 11/2007 | Dalla Betta et al. | JP | 06343644 A2 | 12/1994 |
| 2007/0260242 | A1 | 11/2007 | Dycus et al. | JP | 07265328 A2 | 10/1995 |
| 2007/0265616 | A1 | 11/2007 | Couture et al. | JP | 08056955 A2 | 3/1996 |
| 2008/0004616 | A1 | 1/2008 | Patrick | JP | 08252263 A2 | 10/1996 |
| 2008/0009860 | A1 | 1/2008 | Odom | JP | 09010223 A2 | 1/1997 |
| 2008/0015575 | A1 | 1/2008 | Odom et al. | JP | 11244298 A2 | 9/1999 |
| 2008/0021450 | A1 | 1/2008 | Couture | JP | 2000342599 A2 | 12/2000 |
| 2008/0033428 | A1 | 2/2008 | Artale et al. | JP | 2000350732 A2 | 12/2000 |
| 2008/0039835 | A1 | 2/2008 | Johnson et al. | JP | 2001008944 A2 | 1/2001 |
| 2008/0045947 | A1 | 2/2008 | Johnson et al. | JP | 2001029356 A2 | 2/2001 |
| 2008/0058802 | A1 | 3/2008 | Couture et al. | JP | 2001128990 A2 | 5/2001 |
| 2008/0082100 | A1 | 4/2008 | Orton et al. | SU | 401367 | 11/1974 |

FOREIGN PATENT DOCUMENTS

| | | | | | |
|---|---|---|---|---|---|
| WO | WO89/00757 | 1/1989 | | | |
| DE | 2415263 | 10/1975 | WO | WO 92/04873 | 4/1992 |
| DE | 2627679 | 1/1977 | WO | WO 92/06642 | 4/1992 |
| DE | 8712328 | 3/1988 | WO | WO 94/08524 A | 4/1994 |
| DE | 4303882 | 8/1994 | WO | WO94/20025 | 9/1994 |
| DE | 29616210 | 1/1997 | WO | WO 95/02369 | 1/1995 |
| DE | 19608716 | 4/1997 | WO | WO95/07662 | 3/1995 |
| DE | 19751106 | 5/1998 | WO | WO 95/07662 | 3/1995 |
| DE | 19751108 | 5/1999 | WO | WO95/15124 | 6/1995 |
| EP | 0364216 A1 | 4/1990 | WO | WO96/05776 | 2/1996 |
| EP | 518230 A1 | 12/1992 | WO | WO 96/22056 | 7/1996 |
| EP | 0 541 930 B1 | 5/1993 | WO | WO 96/13218 | 9/1996 |
| EP | 0572131 | 12/1993 | WO | WO 97/00646 | 1/1997 |
| EP | 584787 A1 | 3/1994 | WO | WO 97/00647 | 1/1997 |
| EP | 0589453 A2 | 3/1994 | WO | WO97/10764 | 3/1997 |
| EP | 0623316 A1 | 11/1994 | WO | WO 97/10764 | 3/1997 |
| EP | 0624348 A2 | 11/1994 | WO | WO 97/24073 | 7/1997 |
| EP | 0650701 A1 | 5/1995 | WO | WO 97/24993 | 7/1997 |
| EP | 0694290 A3 | 3/1996 | WO | WO 98/27880 | 7/1998 |
| EP | 0717966 A1 | 6/1996 | WO | WO 99/03407 | 1/1999 |
| EP | 0754437 A3 | 3/1997 | WO | WO 99/03408 | 1/1999 |
| EP | 853922 A1 | 7/1998 | WO | WO 99/03409 | 1/1999 |
| EP | 0875209 A1 | 11/1998 | WO | WO 99/12488 | 3/1999 |
| EP | 0878169 A1 | 11/1998 | WO | WO 99/40857 | 8/1999 |
| EP | 0887046 A3 | 1/1999 | WO | WO 99/40861 | 8/1999 |
| EP | 0923907 A1 | 6/1999 | WO | WO 99/51158 | 10/1999 |
| EP | 0986990 A1 | 3/2000 | WO | WO 99/66850 A | 12/1999 |
| EP | 1034747 A1 | 9/2000 | WO | WO 00/24330 | 5/2000 |
| EP | 1034748 A1 | 9/2000 | WO | WO00/24331 | 5/2000 |
| EP | 1025807 A3 | 10/2000 | WO | WO 00/24331 | 5/2000 |
| EP | 1034746 A3 | 10/2000 | WO | WO 00/41638 | 7/2000 |
| EP | 1050278 A1 | 11/2000 | WO | WO00/47124 | 8/2000 |
| EP | 1053719 A1 | 11/2000 | WO | WO 00/53112 | 9/2000 |
| EP | 1053720 A1 | 11/2000 | WO | WO 01/17448 A | 3/2001 |
| EP | 1055399 A1 | 11/2000 | WO | WO 01/54604 | 8/2001 |
| EP | 1055400 A1 | 11/2000 | WO | WO02/07627 | 1/2002 |
| EP | 1080694 A1 | 3/2001 | WO | WO 02/07627 | 1/2002 |
| EP | 1082944 A1 | 3/2001 | WO | WO 02/067798 A1 | 9/2002 |
| EP | 1159926 A2 | 12/2001 | WO | WO02/080783 | 10/2002 |
| EP | 1301135 A | 4/2003 | WO | WO 02/080783 | 10/2002 |
| EP | 1330991 A1 | 7/2003 | WO | WO02/080784 | 10/2002 |
| EP | 1486177 A2 | 6/2004 | WO | WO 02/080784 | 10/2002 |
| EP | 1472984 A1 | 11/2004 | WO | WO 02/080785 | 10/2002 |
| EP | 1527747 A2 | 5/2005 | WO | WO02/080785 | 10/2002 |
| EP | 1530952 A1 | 5/2005 | WO | WO 02/080786 | 10/2002 |
| EP | 1532932 A1 | 5/2005 | WO | WO02/080786 | 10/2002 |
| EP | 1535581 A2 | 6/2005 | WO | WO 02/080793 | 10/2002 |
| EP | 1609430 A1 | 12/2005 | WO | WO02/080793 | 10/2002 |
| | | | WO | WO 02/080794 | 10/2002 |
| | | | WO | WO02/080794 | 10/2002 |

| WO | WO 02/080795 | 10/2002 |
| WO | WO 02/080796 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO02/081170 | 10/2002 |
| WO | WO 02/081170 | 10/2002 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO2004/073490 | 9/2004 |
| WO | WO 2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |

OTHER PUBLICATIONS

Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.
Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Int'l Search Report EP 06 020574.7 dated Sep. 21, 2007.
Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J. Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001, pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.
Levy et al. "Use of a New Energy-based Vessel Ligation Device During Vaginal Hysterectomy" Int'l Federation of Gynecology and Obstetrics (FIGO) World Congress 1999.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
Chung et al., "Clinical Experience of Sutureless Closed Hemorrhoidectomy with LigaSure" Diseases of the Colon & Rectum vol. 46, No. 1 Jan. 2003.
Strasberg et el., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
W. Scott Helton, "LigaSure Vessel Sealing System: Revolutionary Hemostasis Product for General Surgery" Sales/Product Literature 1999.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al., "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
McLellan et al. "Vessel Sealing for Hemostasis During Gynecologic Surgery" Sales/Product Literature 1999.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
E. David Crawford "Use of a Novel Vessel Seating Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report PCT/US98/18640 dated Dec. 17, 1998.
Int'l Search Report PCT/US98/23950 dated Dec. 29, 1998.
Int'l Search Report PCT/US99/24869 dated Feb. 3, 2000.
Int'l Search Report PCT/US01/11218 dated Aug. 3, 2001.
International Search Report PCT/US01/11224 dated Nov. 13, 2001.
Int'l Search Report PCT/US01/11340 dated Aug. 7, 2001.
Int'l Search Report PCT/US01/11420 dated Oct. 8, 2001.
Int'l Search Report PCT/US02/01890 dated Jul. 17, 2002.
Int'l Search Report PCT/US02/11100 dated Jul. 9, 2002.
Int'l Search Report PCT/USO4/03436 dated Oct. 5, 2004.
Int'l Search Report PCT/USO4/13273 dated Nov. 22, 2004.
Int'l Search Report PCT/USO4/15311 dated Nov. 18, 2004.
Int'l Search Report EP 98944778 dated Oct. 31, 2000.
Int'l Search Report EP 98958575.7 dated Sep. 20, 2002.
Int'l Search Report EP 04027314 dated Mar. 10, 2005.
Int'l Search Report EP 04027479 dated Mar. 8, 2005.
Int'l Search Report EP 04027705 dated Feb. 3, 2005.
Int'l Search Report EP 05013463.4 dated Sep. 28, 2005.
Int'l Search Report EP 05016399 dated Jan. 5, 2006.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.

* cited by examiner

APPARATUS AND METHOD FOR TRANSECTING TISSUE ON A BIPOLAR VESSEL SEALING INSTRUMENT

BACKGROUND

1. Technical Field

The present disclosure relates to electrosurgical instruments used for open and endoscopic surgical procedures for sealing, fusing, or dividing tissue. More particularly, the present disclosure relates to bipolar forceps for sealing vessels, vascular tissues and soft tissues having a blade assembly that is designed to transect tissue while limiting movement of the cutting element.

2. Background of the Invention

Electrosurgical forceps utilize both mechanical clamping action and electrical energy to effect hemostasis by heating the tissue and blood vessels to coagulate and/or cauterize vessels or tissue. However, certain surgical procedures may require sealing blood vessels or vascular tissue rather than just simply effecting hemostasis. "Vessel sealing" or "Tissue Fusion" is defined as the process of liquefying the collagen, elastin and ground substances in the tissue so that it reforms into a fused mass with significantly reduced demarcation between the opposing tissue structures. In contrast, the term "cauterization" is defined as the use of heat to destroy tissue (also called "diathermy" or "electrodiathermy") and the term "coagulation" is defined as a process of desiccating tissue wherein the tissue cells are ruptured and dried. Coagulation of small vessels is usually sufficient to permanently close them. Larger vessels or tissue need to be "sealed" to assure permanent closure. During sealing procedures, surgeons may also divide sealed tissue to ensure that the surrounding tissue heals properly.

Numerous electrosurgical instruments have been proposed in the past for various open and endoscopic surgical procedures. However, most of these instruments cauterize or coagulate tissue and are normally not designed to provide uniformly reproducible pressure on the blood vessel or tissue that, if used for sealing purposes, would result in an ineffective or non-uniform seal. For example, U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cauterizing, and cutting vessels or tissue.

Some of these instruments include blade members or shearing members that simply cut tissue in a mechanical and/or electromechanical manner and are relatively ineffective for vessel sealing purposes. Other instruments generally rely on clamping pressure alone to procure proper sealing thickness and are often not designed to take into account gap tolerances and/or parallelism and flatness requirements, which are parameters that, if properly controlled, can assure a consistent and effective tissue seal. For example, it may be difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied, a thicker less reliable seal is created.

Commonly-owned U.S. application Ser. Nos. PCT Application Serial No. PCT/US01/11340 filed on Apr. 6, 2001 by Dycus, et al. entitled "VESSEL SEALER AND DIVIDER", U.S. application Ser. No. 10/116,824 filed on Apr. 5, 2002 by Tetzlaff et al. entitled "VESSEL SEALING INSTRUMENT" and PCT Application Serial No. PCT/US01/11420 filed on Apr. 6, 2001 by Tetzlaff et al. entitled "VESSEL SEALING INSTRUMENT" teach that to effectively seal tissue or vessels, especially large vessels, two predominant mechanical parameters must be accurately controlled: 1) the pressure applied to the vessel; and 2) the gap distance between the conductive tissue contacting surfaces (electrodes). As can be appreciated, both of these parameters are affected by the thickness of the vessel or tissue being sealed. Accurate application of pressure is important for several reasons: to reduce the tissue impedance to a low enough value that allows enough electrosurgical energy through the tissue; to overcome the forces of expansion during tissue heating; and to contribute to the end tissue thickness which is an indication of a good seal.

As can be appreciated, considerable surgical skill is needed to determine what force is necessary and to accurately apply pressure to the treated tissue. In cases where tissue needs to be divided during the sealing process, the surgical difficulty is compounded by the use of blade assemblies that require lengthy movement such as longitudinal axial movement when the lower and upper jaw members are closed during the procedure. The long cutting motions are problematic in that they may lead to undesirable movement of the cutting element resulting in or promoting an inaccurate seal and/or division of tissue.

SUMMARY

The present disclosure relates to an electrosurgical forceps for sealing tissue, having a pair of jaw members being movable from a first position in spaced relation relative to one another to at least one subsequent position. The jaw members cooperate to grasp tissue therebetween. Each of the jaw members includes an electrically conductive sealing plate adapted to connect to an energy source and configured to communicate energy through tissue held therebetween. At least one of the jaw members includes a blade channel defined therein configured for sliding reception of a surgical blade assembly. The blade channel includes a proximal end, a distal end and a plurality of troughs positioned therebetween. The blade assembly includes a blade body having a plurality of cutting elements extending therealong. Each of the cutting elements includes a cutting edge extendable into the blade channel and a flange extending into each of the troughs. The blade body is selectively movable from a first position where the cutting edges of the cutting elements are spaced relative to the blade channel and the flanges are rest within the troughs to at least one second position where the cutting edges extend within the blade channel.

In some embodiments, at least one of the troughs includes an inclined surface such that proximal movement of the blade body causes the flange to ride along the inclined surface to extend the cutting edge into the blade channel.

In some embodiments, at least one of the troughs is dimensioned such that movement of the blade body causes the flange to move the cutting edge into the blade channel in at least one predetermined direction.

In some embodiments, at least one of the troughs includes a bottom surface and a corresponding flange of the cutting element is dimensioned to include a surface which matingly engages the bottom surface of the trough.

In some embodiments, at least one of the troughs includes a first surface and a second surface, the first surface being dimensioned to move the flange in a first direction upon movement of the blade body relative to the blade channel and a second surface dimensioned to move the flange in a second direction upon movement of the blade body relative to the blade channel.

In some embodiments, the flange and trough are in sliding communication so that movement of the flange in a linear direction along the length of the channel directs the cutting element to move in at least one direction relative to the blade channel.

In some embodiments, the cutting edge of the cutting element is substantially curved. In some embodiments, the cutting edge of the cutting element is substantially straight.

The present disclosure further relates to a surgical blade assembly for electrosurgical forceps including a first jaw member and a second jaw member being moveable thereto. At least one of the jaw members includes a blade channel defined therein having a proximal end, a distal end and a plurality of troughs positioned therebetween. A blade body is dimensioned to slide within the channel. The blade body includes a corresponding plurality of cutting elements each including a cutting edge extendable into the blade channel and a flange extending into one of the troughs. The blade body is selectively movable from a first position where the cutting edges of the cutting elements are spaced relative to the blade channel and the flanges are rest within the troughs to at least one second position wherein the cutting edges extend within the blade channel.

In some embodiments, at least one of the troughs includes an inclined surface such that proximal movement of the blade body causes the flange to ride along the inclined surface to extend the cutting edge into the blade channel.

In some embodiments, at least one of the troughs is dimensioned such that movement of the blade body causes the flange to move the cutting edge into the blade channel in at least one predetermined direction.

In some embodiments, at least one of the troughs includes a bottom surface and a corresponding flange of the cutting element is dimensioned to include a surface which matingly engages the bottom surface of the trough.

In some embodiments, at least one of the troughs includes a first surface and a second surface, the first surface being dimensioned to move the flange in a first direction upon movement of the blade body relative to the blade channel and a second surface dimensioned to move the flange in a second direction upon movement of the blade body relative to the blade channel.

In some embodiments, the flange and trough are in sliding communication so that movement of the flange in a linear direction along the length of the channel directs the cutting element to move in at least one direction relative to the blade channel.

In some embodiments, the cutting edge of the cutting element is substantially curved. In some embodiments, the cutting edge of the cutting element is substantially straight.

The disclosure further relates to a method of cutting tissue which includes providing an electrosurgical forceps for sealing tissue having a pair of jaw members being movable from a first position in spaced relation relative to one another to at least one subsequent position. The jaw members cooperate to grasp tissue therebetween. Each of the jaw members includes an electrically conductive sealing plate adapted to connect to an energy source and configured to communicate energy through tissue held therebetween. At least one of the jaw members includes a blade channel defined therein configured for sliding reception of a surgical blade assembly. The blade channel includes a proximal end, a distal end and a plurality of troughs positioned therebetween. The blade assembly includes a blade body having a plurality of cutting elements extending therealong. Each of the cutting elements includes a cutting edge extendable into the blade channel and a flange extending into each of the troughs. The blade body is selectively movable from a first position where the cutting edges of the cutting elements are spaced relative to the blade channel and the flanges are rest within the troughs to at least one second position where the cutting edges extend within the blade channel. The method includes the steps of positioning the jaw members about tissue and moving the blade body relative to the blade channel such that at least one of the flanges rides along the trough and extends the cutting edges of the cutting elements into and through the tissue.

In some embodiments, the blade body is moved in a proximal direction.

In some embodiments, the blade is moved in a proximal direction and the dimensions of the flange and the trough move the cutting edges of the cutting elements in a substantially angled manner relative to the blade channel.

In some embodiments, the blade is moved in a proximal direction and the dimensions of the flange and the trough move the cutting edges of the cutting elements in a first direction relative to the blade channel to perforate the tissue and then in a second direction to cut the tissue.

DETAILED DESCRIPTION

It has been found that by providing a blade assembly where a blade body is in sliding communication with the blade channel, surgeons can more readily and more easily produce a consistent, high quality tissue transection while limiting movement of the blade and/or end effector assembly. By minimizing movement of the blade and/or end effector assembly during use the surgeon can more accurately divide and/or seal tissue. Furthermore, minimizing movement of the end effector assembly can also reduce thermal spread across or to adjacent tissue. For the purposes herein the term "thermal spread" refers generally to the heat transfer (heat conduction, heat convection or electrical current dissipation) dissipating along the periphery of the electrically conductive or electrically active surfaces to adjacent tissue. This can also be termed "collateral damage" to adjacent tissue.

The configuration of the blade assembly, having a blade that is in sliding communication with at least one surface of the blade channel, will effectively minimize the movement of the blade by providing a predetermined cutting path. For the purposes herein the term "sliding communication" refers generally to two or more surfaces of different structures contacting one another such that the movement of one structure against a second structure will cause the moving structure or structures to move in one or more predetermined directions and/or sequentially in a plurality of directions. In other words, the shape of the surface of one structure will affect the path of movement of another structure sliding against it. Accordingly, in embodiments, the blade body has a predetermined shape that corresponds with the blade channel.

By providing a shaped blade body and a shaped blade channel, the cutting path of the blade will be predetermined such that it influences the efficiency of the tissue cutting and/or limits the movement of the surgical device so that thermal spread/collateral damage to adjacent tissue structures is reduced or eliminated.

Figure 1A:
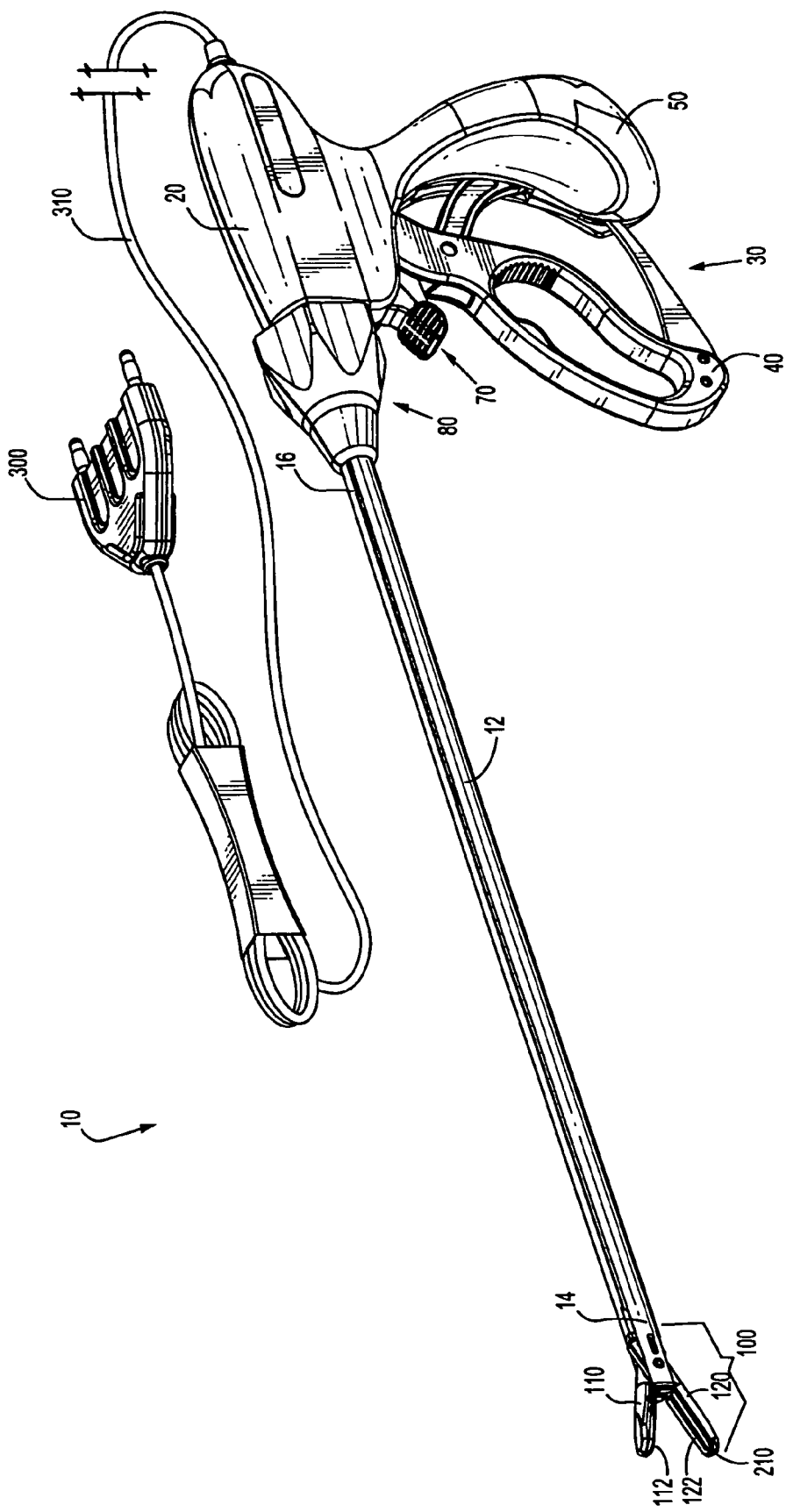
FIG. 1A is a perspective view of an endoscopic bipolar forceps which is configured to support the blade assembly according to the present disclosure.
Figure 1B:
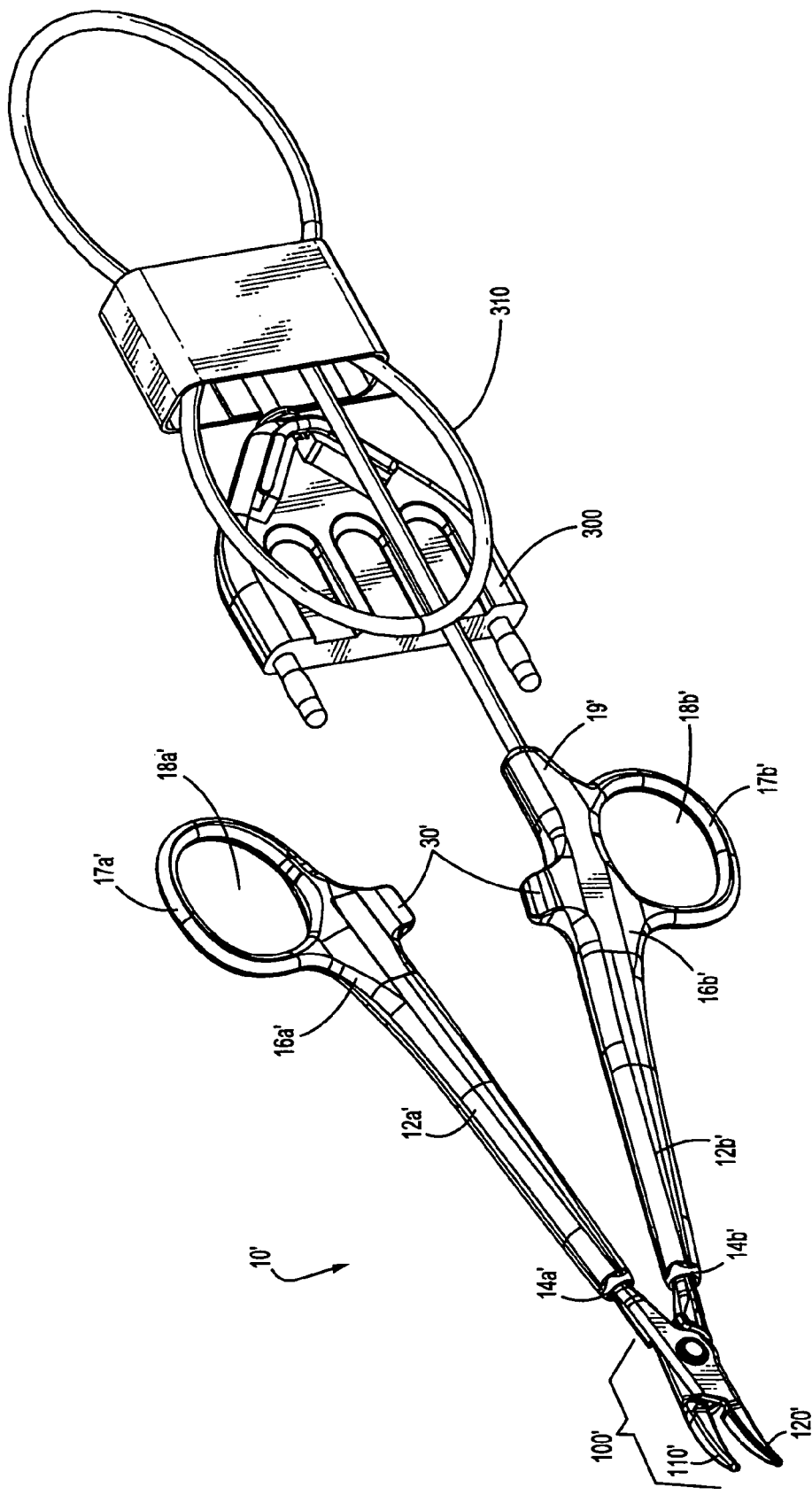
FIG. 1B is a perspective view of an open bipolar forceps which is configured to support the blade assembly according to the present disclosure.

Referring now to FIG. 1A and FIG. 1B, two bipolar forceps 10 and 10' are shown; a first forceps 10 for use with endoscopic surgical procedures and a second forceps 10' for use with open surgical procedures. For the purposes herein, either an endoscopic instrument or an open instrument may be utilized for supporting the blade assembly according to the present disclosure. Obviously, different electrical and mechanical connections and considerations apply to each particular type of instrument; however, the novel aspects with respect to the blade assembly and its operating characteristics remain generally consistent with respect to both the open or endoscopic designs of FIGS. 1A and 1B. Forceps 10 and 10' are shown by way of example and other electrosurgical forceps are also envisioned that may support the blade assembly of the present disclosure. In the drawings and in the description that follows, the term "proximal", as is traditional, will refer to the end of the forceps 10, 10' that is closer to the user, while the term "distal" will refer to the end that is further from the user.

FIG. 1A shows one example of an endoscopic vessel sealing instrument 10 that is configured to support a blade assembly 200 (not explicitly shown). More particularly, forceps 10 generally includes a housing 20, a handle assembly 30, a rotating assembly 80, a trigger assembly 70 and the end effector assembly 100 that mutually cooperate to grasp, seal and, if warranted, divide tissue. The forceps 10 includes a shaft 12 that has a distal end 14 dimensioned to mechanically engage the end effector assembly 100 and a proximal end 16 that mechanically engages the housing 20 proximate the rotating assembly 80.

Forceps 10 also includes a plug 300 that connects the forceps 10 to a source of electrosurgical energy, e.g., an electrosurgical generator (not shown) via an electrical cable 310. Handle assembly 30 includes a fixed handle 50 and a movable handle 40. Handle 40 moves relative to fixed handle 50 to actuate the end effector assembly 100 and enable a user to grasp and manipulate tissue 400 (see FIGS. 8A-D). More particularly, the end effector assembly 100 includes a pair of opposing jaw members 110 and 120 that move in response to movement of the handle 40 from an open position wherein the jaw members 110 and 120 are disposed in spaced relation relative to one another, to a clamping or closed position wherein the jaw members 110 and 120 cooperate to grasp tissue therebetween.

The housing 20 encloses a drive assembly (not explicitly shown) that cooperates with the movable handle 40 to impart movement of the jaw members 110 and 120 from the open position to the clamping or closed position. The handle assembly 30 can generally be characterized as a four-bar mechanical linkage that provides a unique mechanical advantage when sealing tissue between the jaw members 110 and 120. For example, once the desired position for the sealing site is determined and the jaw members 110 and 120 are properly positioned, handle 40 may be compressed fully to lock the jaw members 110 and 120 in a closed position against the tissue. Further, should it be determined that tissue should be divided, trigger assembly 70 may be compressed to actuate the blade assembly, in accordance with the present disclosure, located in blade channel 210 in end effector assembly 100. Other force activating assemblies and trigger mechanisms are envisioned that may be used in connection with the blade assemblies described herein. When the jaw members 110 and 120 are fully compressed about the tissue, the forceps 10 is now ready for selective application of electrosurgical energy and/or tissue division.

Experimental results suggest that the magnitude of pressure exerted on the tissue by the electrically conductive sealing surfaces 112, 122 of the jaw members 110 and 120, respectively, is important in assuring a proper surgical seal. Pressures within a working range of about 3 $kg/cm^2$ to about 16 $kg/cm^2$ and, preferably, within a working range of about 6 $kg/cm^2$ to about 13 $kg/cm^2$ have been shown to be effective for sealing various tissue types. Pressures within a working range of about 4.5 $kg/cm^2$ to about 8.5 $kg/cm^2$ may be optimal for sealing particular tissue types.

An open forceps 10' for use in connection with traditional open surgical procedures and is shown by way of example in FIG. 1B. Open forceps 10' includes a pair of elongated shaft portions 12a', 12b' each having a proximal end 16a' and 16b', respectively, and a distal end 14a' and 14b', respectively. The forceps 10' includes jaw assembly 100' that attaches to the distal ends 14a' and 14b' of shafts 12a' and 12b', respectively. Jaw assembly 100' includes an upper jaw member 110' and a lower jaw member 120' that are movable relative to one another to grasp tissue therebetween.

Still referring to FIG. 1B, each shaft 12a' and 12b' includes a handle 17a' and 17b' disposed at the proximal end 16a' and 16b' thereof, which each define a finger hole 18a' and 18b', respectively, therethrough for receiving a finger of the user. As can be appreciated, finger holes 18a' and 18b' facilitate movement of the shafts 12a' and 12b' relative to one another that, in turn, pivot the jaw members 110' and 120' from the open position wherein the jaw members 110' and 120' are disposed in spaced relation relative to one another for manipulating tissue to a clamping or closed position wherein the jaw members 110' and 120' cooperate to grasp tissue therebetween.

A ratchet 30' is included for selectively locking the jaw members 110' and 120' relative to one another at various positions during pivoting. In embodiments, each position associated with the cooperating ratchet interfaces 30' holds a specific, i.e., constant, strain energy in the shaft members 12a' and 12b' that, in turn, transmits a specific closing force to the jaw members 110' and 120'. The ratchet 30' may include graduations or other visual markings that enable the user to easily and quickly ascertain and control the amount of closure force desired between the jaw members 110' and 120'. One of the shafts, e.g., 12b', includes a proximal shaft connector/flange 19' that is designed to connect the forceps 10' to a source of RF energy (not shown) via an electrosurgical cable 310 and plug 300.

As mentioned above, two mechanical factors play an important role in determining the resulting thickness of the sealed tissue and effectiveness of the seal, i.e., the pressure applied between opposing jaw members 110' and 120' and the gap between the opposing jaw members 110' and 120' during the sealing process. Applying the correct force is also important for other reasons: to reduce the impedance of the tissue to a low enough value that allows enough current through the tissue; and to overcome the forces of expansion during the heating of the tissue in addition to contributing towards creating the required seal thickness necessary for a good seal.

For the purposes herein, electrode assemblies 100 and 100' include the same general configuration and are designed so that surgeons can more readily and more easily produce consistent, high quality tissue transections while limiting movement of the blade and/or end effector assembly. However, certain modifications may have to be made to each electrode sealing assembly 100 (or 100') to fit the electrode sealing assembly 100 (or 100') with blade assembly 200 to a specific support structure for an open or endoscopic instrument. By controlling the intensity, frequency and duration of the RF energy applied to the tissue, the user can selectively seal the tissue as needed for a particular purpose. As can be appreciated, different tissue types and the physical characteristics associated with each tissue type may require different electrical sealing and/or cutting parameters.

Figures 2A, 2B, 2C:
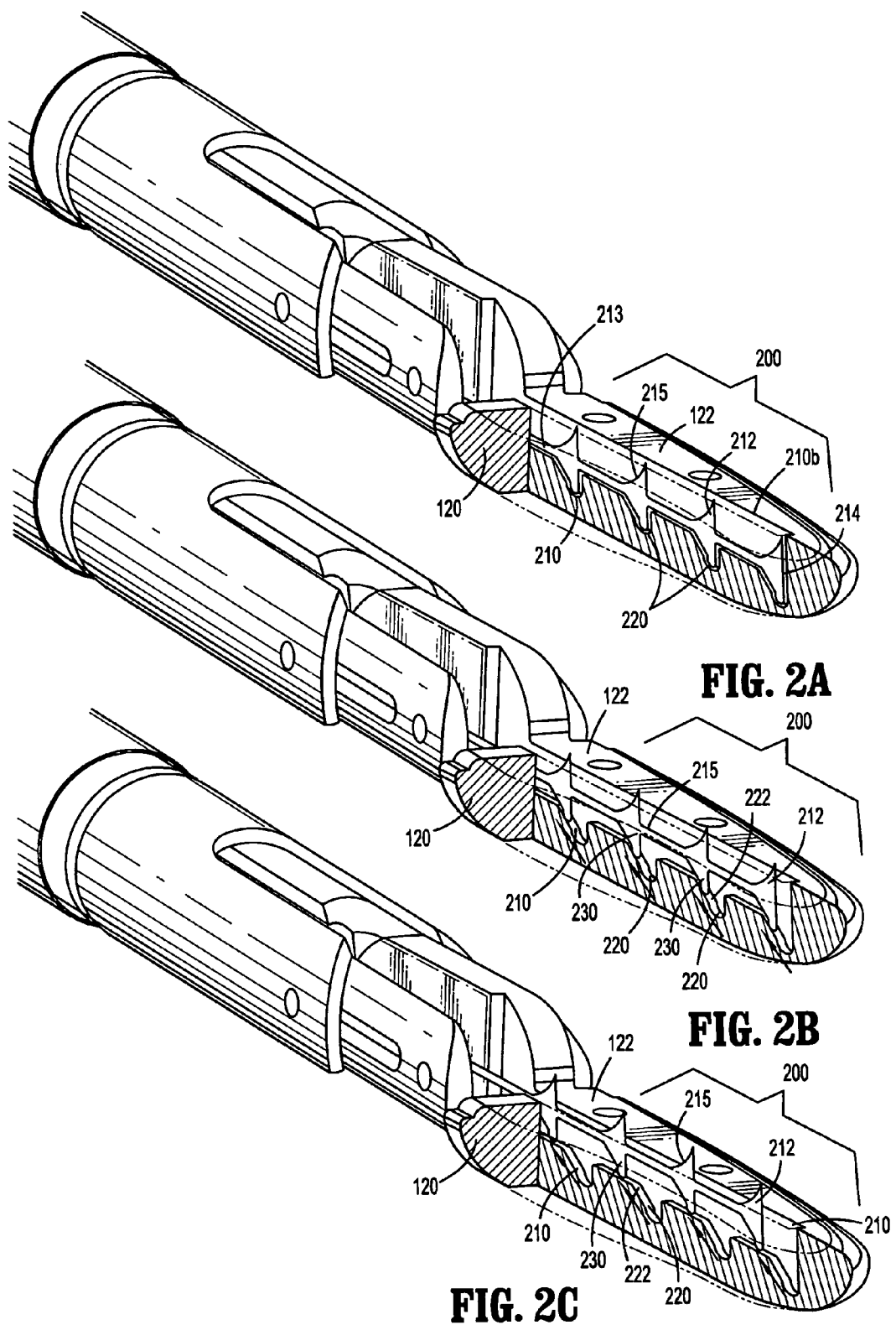
FIG. 2A is a greatly-enlarged, front perspective view of the bottom jaw member of the end effector assembly of FIG. 1A showing the blade of the blade assembly in a distal-most or unactuated position.
FIG. 2B is a greatly enlarged, front perspective view of the bottom jaw member of FIG. 1A showing the position of the blade after being slightly actuated.
FIG. 2C is a greatly enlarged, front perspective view of the bottom jaw member of FIG. 1A showing the position of the blade after being fully actuated in a proximal-most or fully actuated position.

FIGS. 2A, 2B and 2C show enlarged views of the lower jaw 120 of the electrode sealing assembly 100 (or 100') according to the present disclosure. The front portion of lower jaw member 120 is cut away to show blade channel 210 in the center portion of the lower jaw member 120 below the lower sealing surface 122. In one embodiment, a second jaw 110 with similar components as described is positioned in opposition to jaw member 120. Only the elements of jaw member 120 are described herein; however, jaw member 110 may also include identical and/or similar elements that are designed to accomplish similar purposes such that bipolar electrosurgical energy can be conducted through tissue held between the two jaw members 110 and 120 to effect a seal and/or division of tissue.

Referring now to FIG. 2A, lower jaw member 120 includes a blade assembly 200 in accordance with one embodiment of the present disclosure. The front portion of lower jaw member 120 is cut away to show blade channel 210 in the center portion of the lower jaw member 120 below the lower sealing surface 122. More particularly, lower jaw member 120 includes a blade assembly 200 having a blade channel 210 formed when the jaw members 110 (not shown in FIG. 2A) and 120 are closed. In other words, in embodiments, the blade channel 210 includes two blade channel halves—blade channel half 210a disposed in sealing plate 112 of jaw member 110 (not shown in FIG. 2A) and blade channel half 210b in sealing plate 122 of jaw member 120. Blade channel 210 extends through the longitudinal midline of jaw member 120. The blade channel 210 may be configured as a straight slot with no degree of curvature or, alternatively, blade channel 210 may be dimensioned to include some degree of curvature. Blade channel 210 also includes one or more troughs 220 in the longitudinal bottom portion of blade channel 210. Recessed within the blade channel 210 lies blade 212 having a proximal end 213, a distal end 214, and a cutting edge 215 extending between the proximal and distal ends. As best seen in FIG. 2A, blade 212 is in a distal-most or unactuated position. Accordingly, the distal end 214 is in its distal-most position, and cutting edge 215 does not rise above or out of sealing surface 122.

Referring now to FIG. 2B, blade 212 is shown after being slightly actuated. More particularly, and with respect to the blade movement, one or more flanges 230 are positioned opposite cutting edge 215 of blade 212. Flange 230 of blade body 212 contacts the bottom of the blade channel 210 and is positioned in one or more troughs 220. The trough 220 may be configured as a ramp with very little curvature. In other words, the proximal wall 222 of trough 220 may be a beveled edge. Alternatively, proximal wall 222 of trough 220 may be configured as a ramp with curvature. As seen in FIG. 2B, when blade assembly 200 is slightly activated, flange 230 moves proximally to a position immediately adjacent or upon proximal wall 222. Consequently, cutting edge 215 rises above or out of sealing surface 122.

Referring now to FIG. 2C, blade 212 is shown in a fully actuated position. More particularly, flange 230 of blade body 212 contacts the top of trough 220 or the most distal portion of proximal wall 222 of trough 220. As blade 212 is fully activated, and placed into its fully extended position, cutting edge 215 of the blade 212 moves up and out of lower sealing surface 122, as well as proximal to the distal edge of blade channel 210. The blade can be moved in a first upwards direction to perforate tissue, then in a second proximal direction to cut across the tissue. Accordingly, the blade 212 and trough 220 may be dimensioned to move in one or more predetermined distances and/or directions depending on a particular purpose.

Figure 3A:
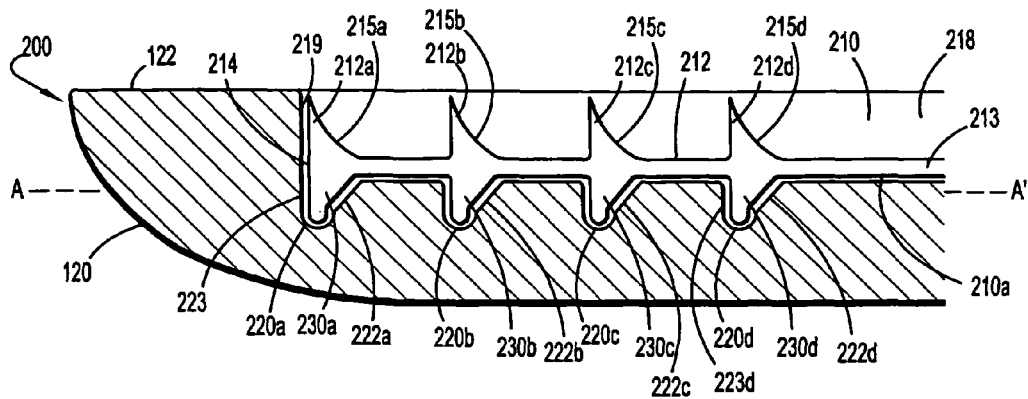
FIG. 3A is a schematic graphic illustration of the blade assembly of FIG. 2A in a distal-most or unactuated position.
Figure 3B:
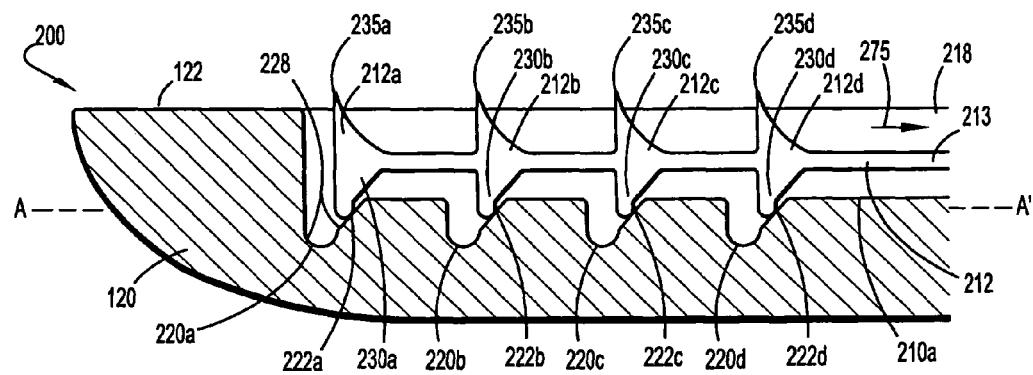
FIG. 3B is a schematic graphic illustration of the blade assembly of FIG. 2B showing the position of the blade after being slightly actuated.
Figure 3C:
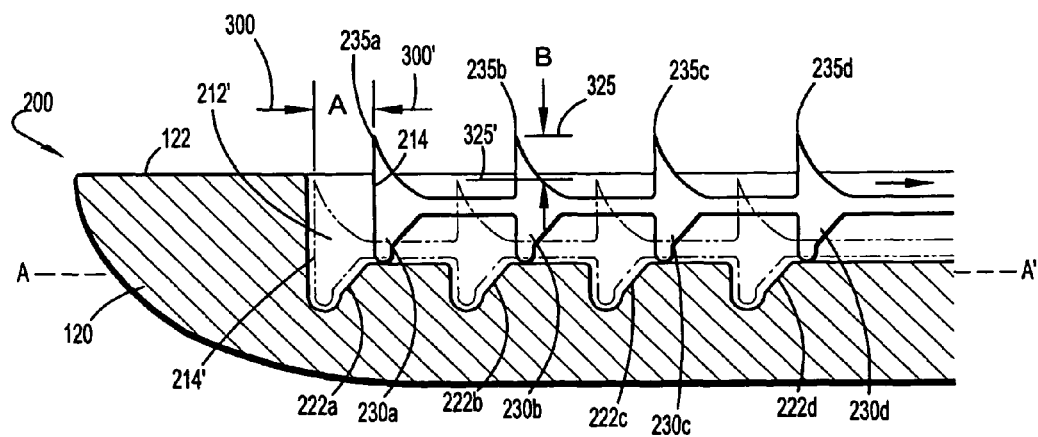
FIG. 3C is a schematic graphic illustration of the blade assembly of FIG. 2C showing the position of the blade after being fully actuated.

FIGS. 3A, 3B and 3C show enlarged schematic cross-sectional side views of the lower jaw 120 of the electrode sealing assembly 100 (or 100') according to the present disclosure. Blade 212 may be dimensioned to include a plurality of individual cutting elements 212a, 212b, 212c and 212d disposed along the blade shaft of blade body 212. Any suitable number of cutting elements 212 may be utilized to suit a particular surgical purpose. Likewise, a corresponding number of blade troughs 220a-d may be utilized to cooperate with the cutting elements 212a-212d to transect tissue.

With particular respect to FIGS. 3A-3C, a single cutting element 212a and trough 220a will be explained in detail along with the operations thereof. As mentioned above, blade assembly 200 includes a blade channel defined therein. Blade channel 210 is shown having a proximal end 218, a distal end 219 and one or more troughs 220a-220d positioned between the proximal and distal ends. In each trough, for example, trough 220a has a corresponding proximal wall 222a, a distal wall 223a, and a predetermined depth. The proximal wall 222a of trough 220a has a predetermined shape and/or may be configured as a straight edge with no degree of curvature. Alternatively, proximal wall 222a of the trough 220a may be dimensioned to include some degree of curvature. Blade body 212 includes a proximal end 213, a distal end 214, and a cutting element 212a-212d extending between the proximal and distal ends. Each cutting element 212a-212d includes a flange 230a-230d positioned opposite a corresponding cutting edge 215a-215d. Flanges 230 are disposed adjacent corresponding troughs 220 such that each cutting element 212a-212d is in sliding communication with the channel 210. Accordingly, movement of blade 212 in a proximal direction will cause flanges 230a-230d to slide against the proximal walls of the troughs 222a-222d causing the cutting element 212a-212d to move in one or more predetermined directions and/or sequentially in a plurality of directions.

Referring now to FIG. 3A, blade 212 is in a distal-most or unactuated position. Accordingly, the distal end 214 is in its distal-most position and immediately adjacent to the distal end 219 of blade channel 210. Consequently, cutting edge 215 does not rise above or out of sealing surface 122.

Referring now to FIG. 3B, as the blade is actuated, flanges 230a-230d contact proximal ends 222a-222d of troughs 220a-220d. In one envisioned embodiment, trough 220 may be configured to have a receptacle 228 at the bottom portion thereof. In other words, the bottom of trough 220 may be rounded such that flange 230a-230d rest within the trough 220a-220d when the cutting elements are unactuated, and quickly extend the cutting elements 212a-212d into the tissue when the blade 212 is actuated. For example, the rounded portion of the troughs may have an incline of about 50 degrees to 90 degrees off of the longitudinal central axis A-A' to initially urge the blade into tissue. The proximal ends of the troughs may have an incline of about 10 degrees to 70 degrees off of the longitudinal central axis A-A' to facilitate cutting. Moreover, different troughs, e.g. trough 220a, may have a different initial angle than another trough 220d.

Still referring to FIG. 3B, when the blade 212 and blade channel 210 are in sliding communication, blade 212 is directed in at least two sequential directions when actuated in a proximal direction as shown by arrow 275. For example, initial activation may direct blade 212 in a first direction, which may be substantially upward, and sequential activation may direct blade 212 in a substantially proximal direction. Accordingly, the predetermined shape of troughs 220a-220d will cause the blade to move in one or more predetermined directions. Proximal wall 222 may have many suitable shapes, inclines, and depths in order to direct blade 212. In this case, activation in the direction of arrow 275 causes cutting points 235a-235d to rise above or out of sealing surface 122. As best shown in FIG. 8C, this initial first movement is well suited for perforating or puncturing tissue disposed upon lower sealing surface 122.

Referring now to FIG. 3C, compressing movement of the activator 70 (not shown in FIG. 3C) moves blade 212 to a proximal-most position to complete the cutting stroke. As such, flanges 230a-230d are pushed to the top of proximal wall of trough 222a-222d. Blade 212' is shown in phantom to show the difference between an unactuated blade 212 (FIG. 3A) and a fully actuated blade (FIG. 3C). As shown by distance "A" between arrow 300 and 300', the distal edge 214 moves in a proximal direction. Distance "A" may be in the range of about 5 mm to about 1 cm. As shown by distance "B" between arrow 325 and 325', the cutting points 235a-235d move in an upward direction in a range of about 5 mm to about 1 cm.

FIGS. 4A, 4B, 4C and 4D show enlarged schematic side views of the various blades 312, 412, 512, and 612 of the electrode sealing assembly 100 (or 100') according to the present disclosure. For example, blade 312 has a predetermined shape having a top cutting edge 315 and a bottom edge 357 that corresponds with the blade channel 310 (not shown). The length of the blade 312 is also predetermined depending on factors such as the size of the end effector assembly it will be assembled into and/or the type of tissue the forceps are suitable for cutting. In embodiments, the length of the blade is selected to fit effector assembly having jaws the length of about 3.5 cm. In embodiments, blade 312 has a length of about 0.5 cm to about 5 cm. The blade 312 may be configured to have one or more cutting elements 316, which extend away from the central longitudinal axis A-A' of the cutting blade 312. Each cutting element may have a substantially flat face 317 that extends from the blade body 312, the flat face terminating at a cutting point 335. The flat face has a width that is thin enough to be recessed inside the blade channel 310 (not shown in FIGS. 4A, 4B, 4C and 4D). The flat face may have a width of from about 1 mm to about 100 mm. In embodiments, the flat face may have a width of from about 10 mm to about 30 mm. The flat face has a second cutting edge 340 positioned between the cutting point 335 and the top of the blade shaft 385. The proximal edge of the flat face may have a sharp edge to form a second cutting edge 340. The second cutting edge 340 may be configured as a straight edge with no degree of curvature between the cutting point and the top of the blade shaft 385. Alternatively, second cutting edge may be dimensioned to include some degree of curvature between the cutting point 340 and the top of the blade shaft 385.

The blade 312 may be configured to have one or more flanges 330 that extend away from the central longitudinal axis A-A' of the cutting blade 312. Each flange may have a substantially flat surface 332 and extend from the blade body 312, the flat surface terminating at an edge or point 334. The flat surface has a width that is thin enough to be recessed inside the blade channel 310 (not shown in FIGS. 4A, 4B, 4C and 4D). In some embodiments, the flat surface may have a width of from about 1 mm to about 100 mm. In some embodiments, the flat surface may have a width of from about 10 mm to about 30 mm. The flat surface has a proximal edge 350 positioned between the edge or point 334 and the bottom of the blade shaft 390. The proximal edge of the flange 350 may be configured as a straight edge with no degree of curvature between the edge or point 334 and the bottom of the blade shaft 390. Alternatively, proximal edge of the flange 350 may be dimensioned to include some degree of curvature between the cutting point and the bottom of the blade shaft 390.

Figure 4A:
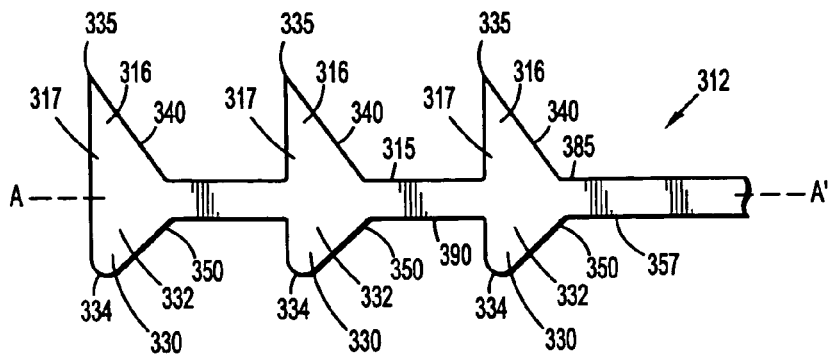
FIG. 4A is a side view of a first blade suitable for use in accordance with the present disclosure.

Referring now to FIG. 4A, the flat face 317 has a second cutting edge 340 positioned between the cutting point 335 and the top of the blade shaft 385. In other words, the proximal edge of the flat face 317 has a sharp edge forming a second cutting edge 340. Here second cutting edge 340 is configured as a straight edge with substantially no degree of curvature between the cutting point 335 and the top of the blade shaft 385. Further, the flat surface of the flange 330 has a proximal edge 350 positioned between the edge or point 334 and the bottom of the blade shaft 390. The proximal edge of the flange 350 is configured as a straight edge with substantially no degree of curvature between the edge 334 and the bottom of the blade shaft 390. Edge 334 is also shown as a substantially round or curved edge.

Figure 4B:
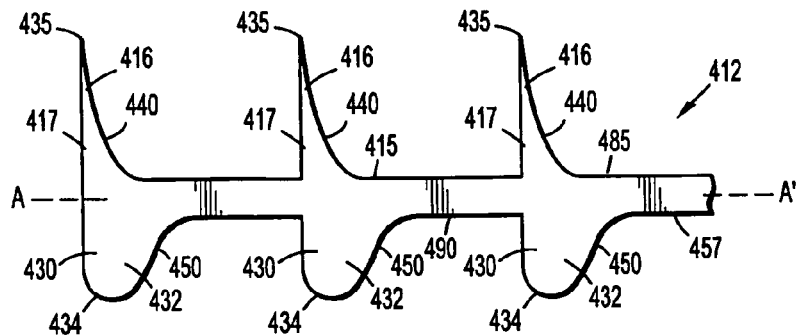
FIG. 4B is a side view of a second blade suitable for use in accordance with the present disclosure.

Referring now to FIG. 4B, an enlarged schematic side view of another blade 412 of the electrode sealing assembly 100 (or 100') according to the present disclosure is shown. The shape and dimensions of the blade is predetermined in that the cutting edge, number of cutting teeth, and troughs may vary depending on a number of factors, including, the types of tissue to be cut, dimensions of the jaw member, and dimensions of the blade channel (not shown in FIG. 4B). Here the blade 412 has more than one cutting teeth 416 extending from the longitudinal axis of the blade; more specifically three teeth extend from the axis A-A'. However, a plurality of cutting teeth may extend from axis A-A' such as 1 to 50 cutting teeth 416. Still referring to FIG. 4B, blade 412 has a corresponding number of flanges extending from the longitudinal axis of the blade A-A', more specifically three flanges extend from the axis. The number of flanges 430 may be different than the number of cutting edges 416. The flat face 417 has a second cutting edge 440 positioned between the cutting point 435 and the bottom of the top of the blade shaft 485. The proximal edge of the flat face 417 has a sharp edge forming a second cutting edge 440. The second cutting edge 440 is configured as a substantially curved edge with substantially a high degree of curvature between the cutting point and the longitudinal axis A-A'. Further, the flat surface 445 of the flange has a proximal edge 450 positioned between the edge or point 434 and the bottom of the blade shaft 490. The proximal edge of the flange 450 is configured as a curved edge with a substantially high degree of curvature between the edge 434 and the longitudinal axis A-A' of the blade such that an arc is formed having a proximal center. Edge 434 is also shown as a substantially round or curved edge.

Figure 4C:
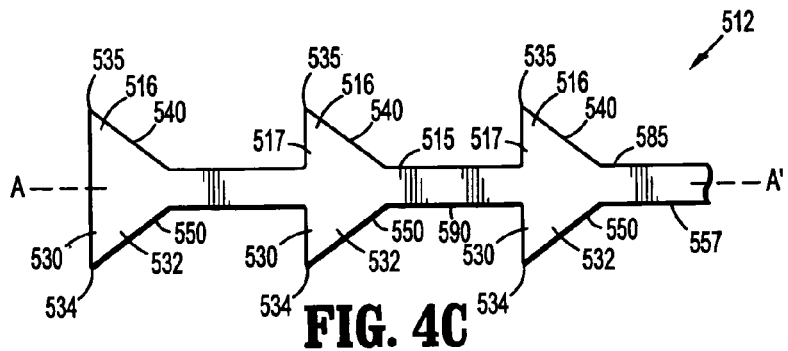
FIG. 4C is a side view of a third blade suitable for use in accordance with the present disclosure.

Referring now to FIG. 4C, another embodiment of blade 512 is shown. The second cutting edge 540 is configured as a substantially straight edge with substantially no degree of curvature between the cutting point and the top of the blade shaft 585. Furthermore, the flat surface of the flange has a proximal edge 550 positioned between the edge or point 534 and the bottom of the blade shaft 590. The proximal edge of the flange 550 is configured as a straight edge with no degree of curvature between the edge 534 and the bottom of the blade shaft 590. Edge 534 is also shown as a point.

Figure 4D:
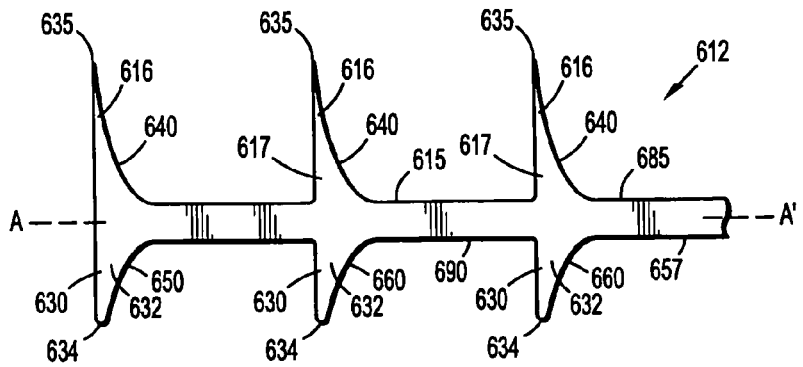
FIG. 4D is a side view of a fourth blade suitable for use in accordance with the present disclosure.

Referring now to FIG. 4D, yet another envisioned blade design 612 is shown. The second cutting edge 640 is configured as a substantially curved edge with substantially a high degree of curvature between the cutting point 635 and the top of the blade shaft 685 such that an arc is formed having a distal center. Furthermore, the flat surface of the flange has a proximal edge 650 positioned between the edge or point 634 and the bottom of the blade shaft 690. The proximal edge of the flange 650 is configured as a curved edge with a substantially high degree of curvature between the edge 634 and the bottom of the blade shaft 690 such that an arc is formed having a distal center. Edge 634 is also shown as a substantially round or curved edge.

Figure 5:
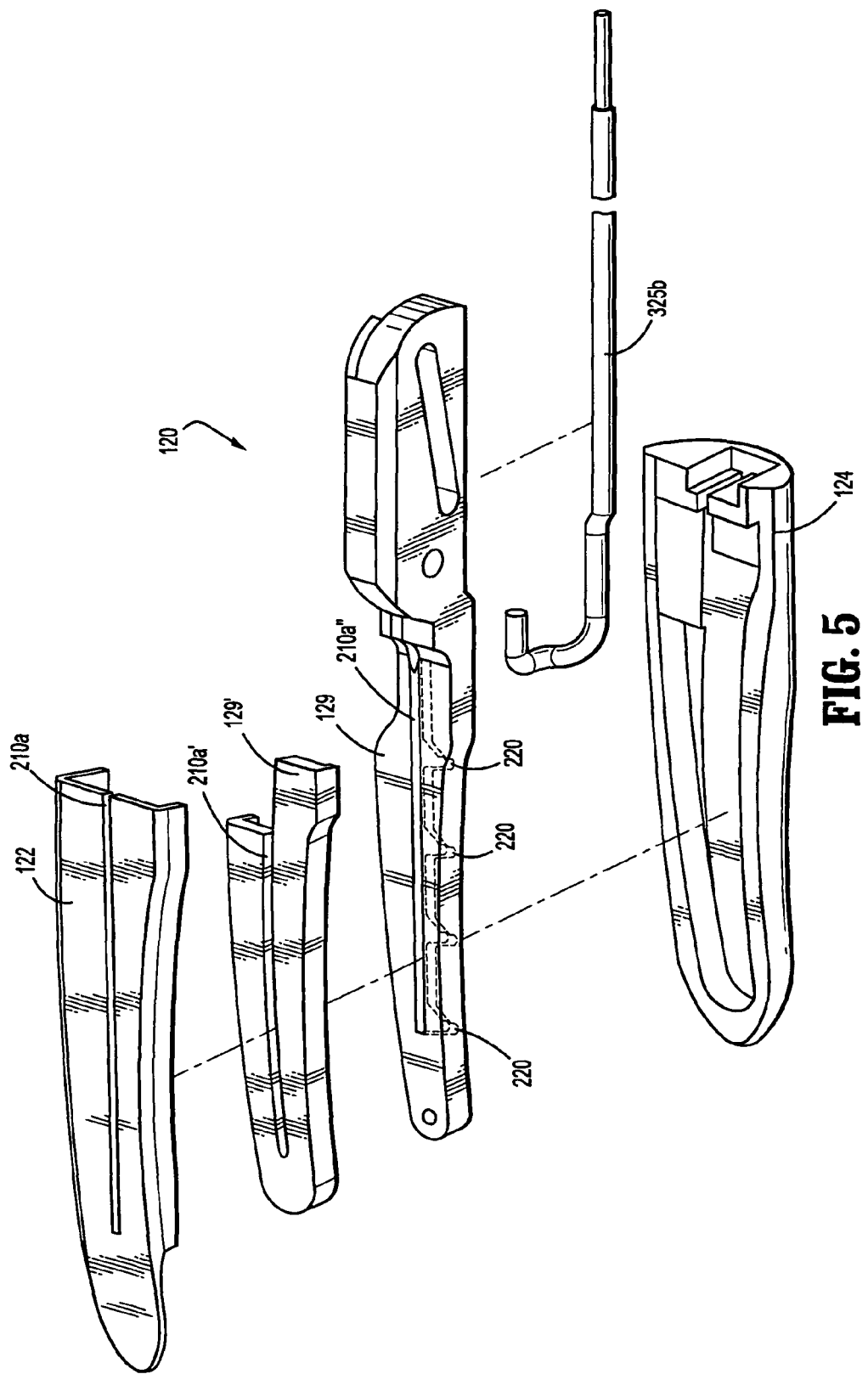
FIG. 5 is a greatly-enlarged, perspective view of the bottom jaw of the end effector assembly of FIG. 1A with parts separated.

As illustrated in FIG. 5, jaw member 120 includes a jaw housing 124 that encapsulates a support plate 129, an insulator plate 129' and an electrically conductive sealing surface 122. Likewise, the electrically conductive surface 122, insulator plate 129', and support plate 129 when assembled, include respective longitudinally-oriented blade channels 210a, 210a', and 210a" defined therethrough for reciprocation of the blade 212 (not shown in FIG. 5). As best seen in FIG. 5, the bottom of plate channel 210a is formed from the surface of support plate 129. Accordingly, troughs 220 are cut out of the surface of support plate 129.

Figure 6:
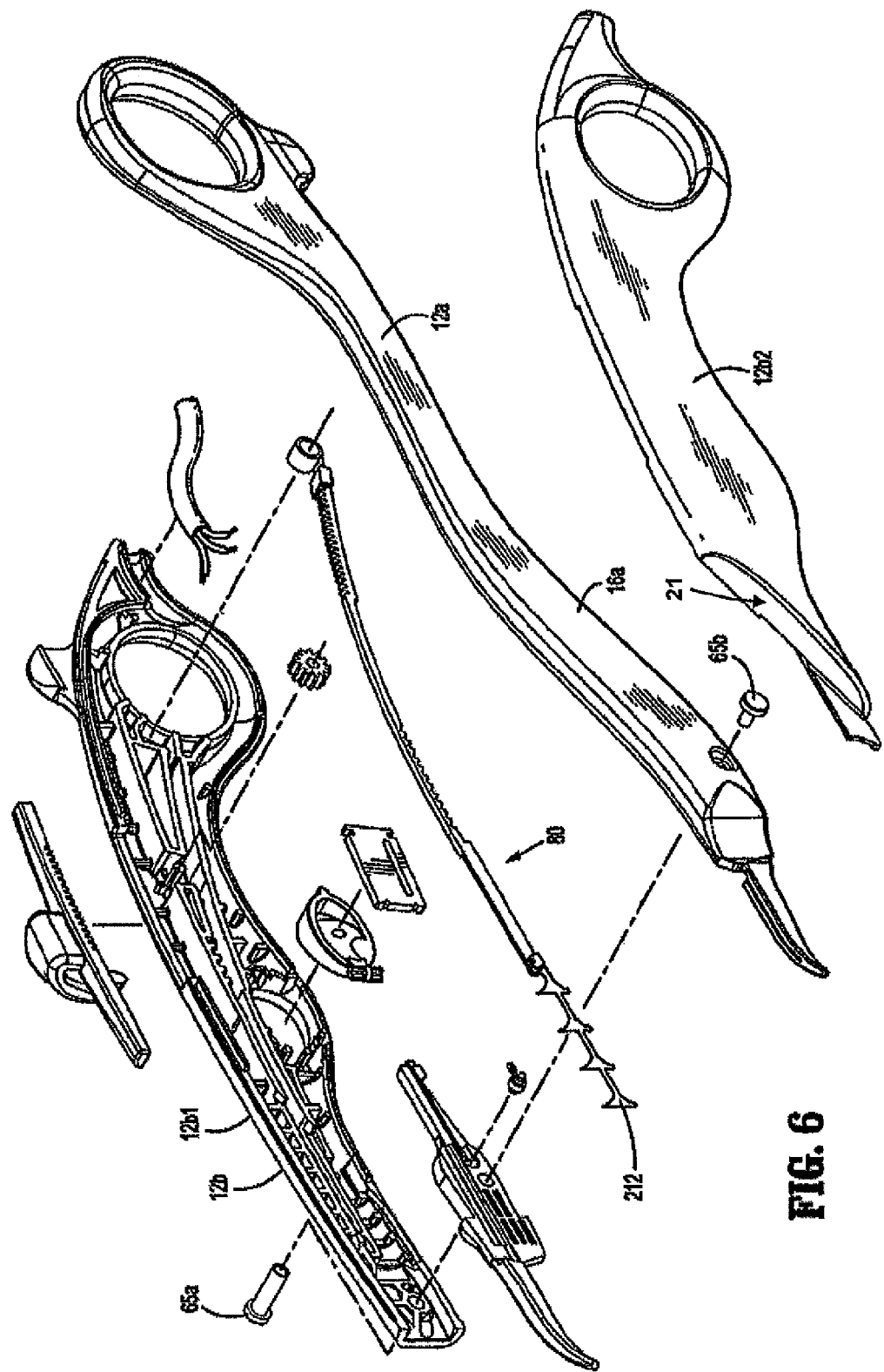
FIG. 6 is a perspective view of the forceps of FIG. 1B with parts separated.

Referring now to FIG. 6, an open bipolar forceps is configured to support blade 212. Shaft 12b is constructed from two components, namely, 12b1 and 12b2, which matingly engage one another about the distal end 16a of shaft 12a to form shaft 12b. The two component halves 12b1 and 12b2 may be ultrasonically-welded together at a plurality of different weld points or the component halves 12b1 and 12b2 may be mechanically engaged in any other suitable fashion, such as snap-fit, glued, screwed, etc. After component halves 12b1 and 12b2 are welded together to form shaft 12b, shaft 12a is secured about pivot 65 and positioned within a cut-out or relief 21 defined within shaft portion 12b2 such that shaft 12a is movable relative to shaft 12b. More particularly, when the user moves the shaft 12a relative to shaft 12b to close or open the jaw members 110 and 120, the distal portion of shaft 12a moves within cutout 21 formed within portion 12b2. Blade 212 is shown attached to cutting mechanism 80. The device can be actuated to move blade 212 in a proximal and/or distal direction.

Figure 7A:
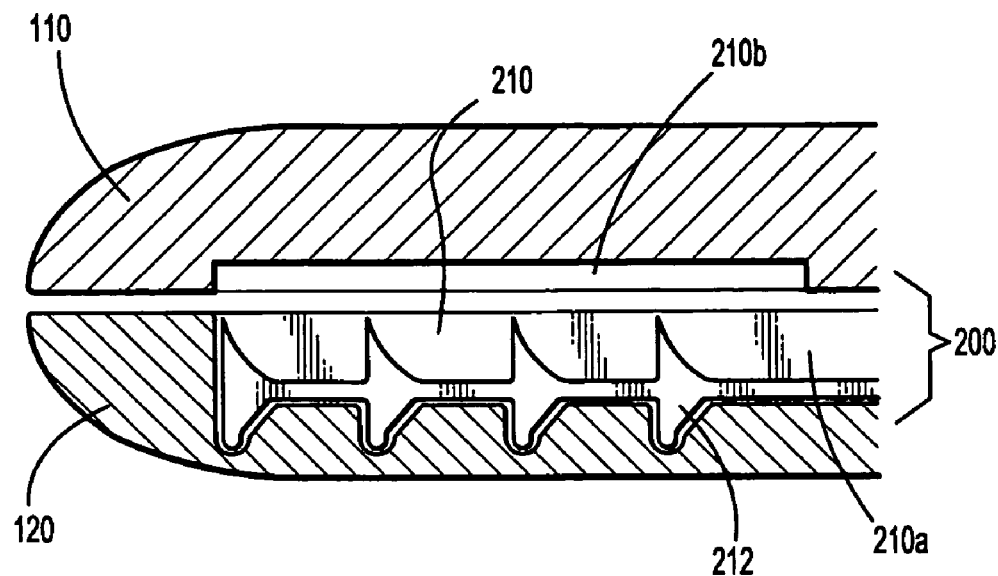
FIG. 7A is a greatly-enlarged schematic, side cross sectional view of the end effector assembly of FIG. 1A shown in a closed configuration with blade in bottom jaw.
Figure 7B:
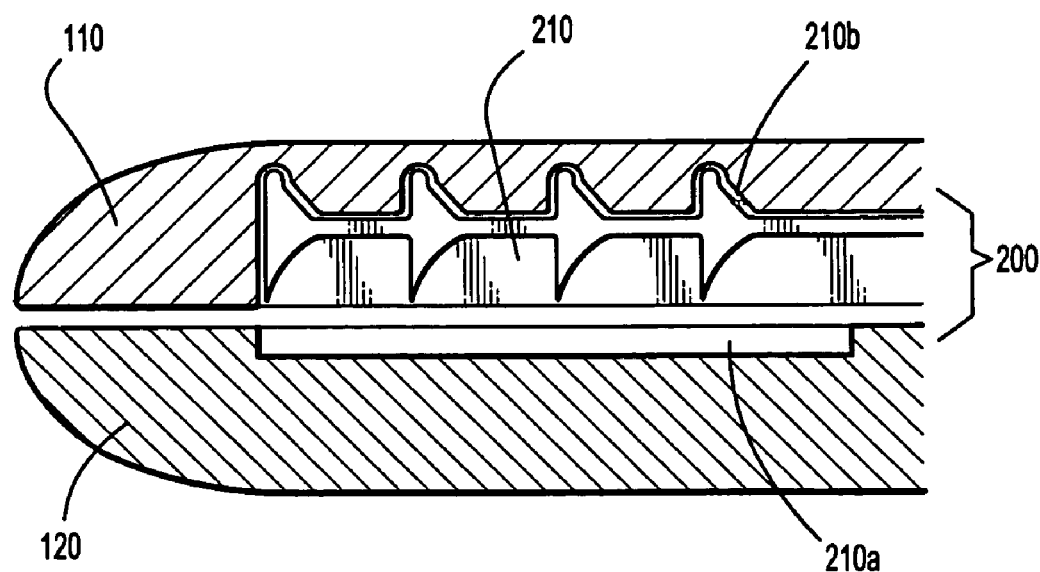
FIG. 7B is a greatly-enlarged schematic, side cross sectional view of the end effector assembly of FIG. 1A shown in a closed configuration with blade in top jaw.

Referring now to FIGS. 7A and 7B, when the blade 212 is in an unactuated position and fully recessed, it can be located within either of jaw members 110 and 120. As best seen in FIG. 7A, blade 212 is shown in lower jaw member 120, and the empty blade channel half 210b is disposed in jaw member 110. As best seen in FIG. 7B, blade 212 is shown in upper jaw member 110, and the empty blade channel half 210a is disposed in jaw member 120. The positioning of the blade is predetermined depending upon, among other things, the needs and desires of the surgeon.

Referring now to FIGS. 8A, 8B, 8C and 8D, electrosurgical forceps for sealing tissue are shown having an upper jaw member 110 and a lower jaw member 120. Axis 850 is shown to represent that the jaw members are movable from a first position in spaced relation relative to one another to at least one subsequent position. Accordingly, the jaw members are movable and cooperate to grasp tissue therebetween.

As described above, at least one of the jaw members has a blade 210 channel defined along a length thereof. One or more of the jaw members includes a surgical blade assembly 200 including a blade channel 210 having a proximal end, a distal end and one or more troughs 220 positioned between the proximal and distal ends. A blade body 212 having a proximal end, a distal end, and a cutting edge 215 extends between the proximal and distal ends, and one or more flanges 230 are positioned opposite the cutting edge 215. As described above, the flanges 230 are disposed within the one or more troughs 220 such that the blade body 212 is in sliding communication with the blade channel 210.

Figure 8A:
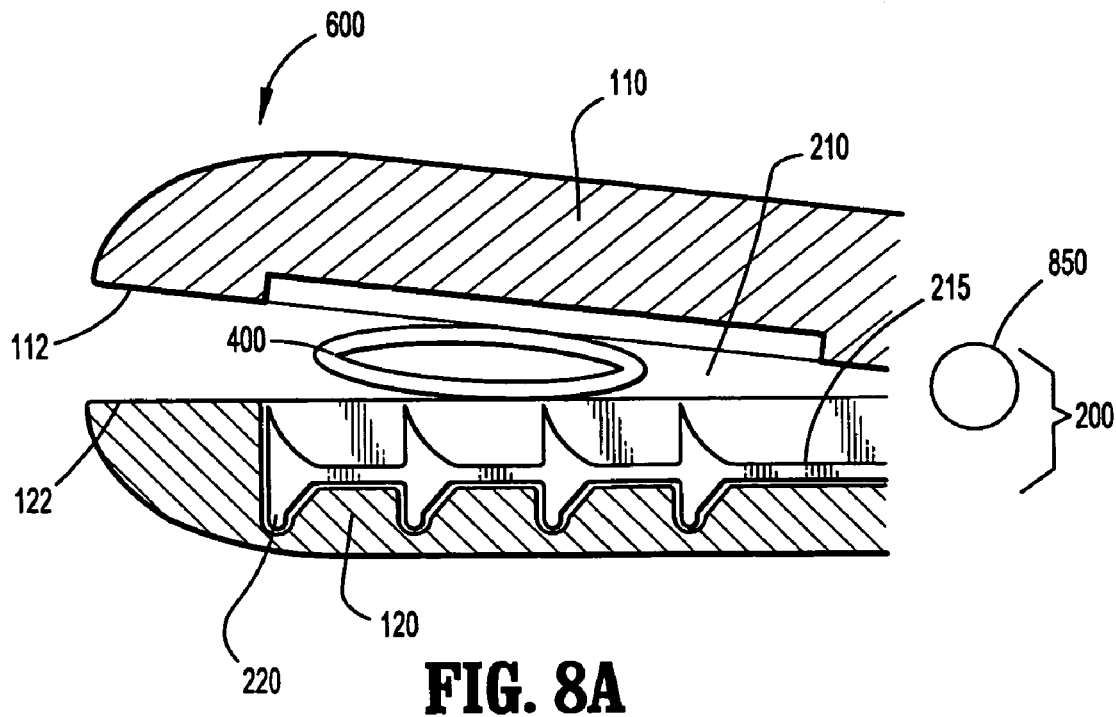
FIG. 8A is a greatly-enlarged schematic, side cross sectional view of the end effector assembly of FIG. 1A shown in an open configuration with tissue therein.

Referring now to FIG. 8A, the jaw members 110 and 120 are shown by arrow 600 being moved from a first position in spaced relation relative to one another to at least one subsequent position. As shown, the jaw members 110 and 120 are being moved to grasp tissue 400 therebetween. Each of the jaw members includes an electrically conductive sealing plate 112, 122, which communicates electrosurgical energy through tissue 400 held therebetween when the forceps is activated.

Figure 8B:
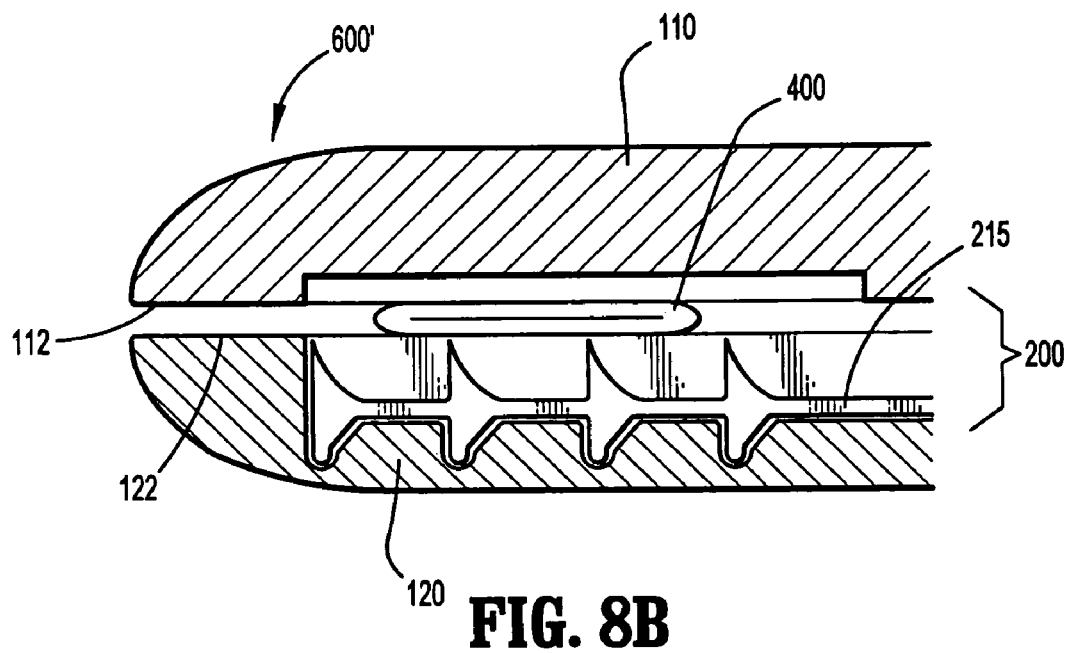
FIG. 8B is a greatly-enlarged schematic, side cross sectional view of the end effector assembly of FIG. 1A shown in a closed configuration with tissue therein.
Figure 8C:
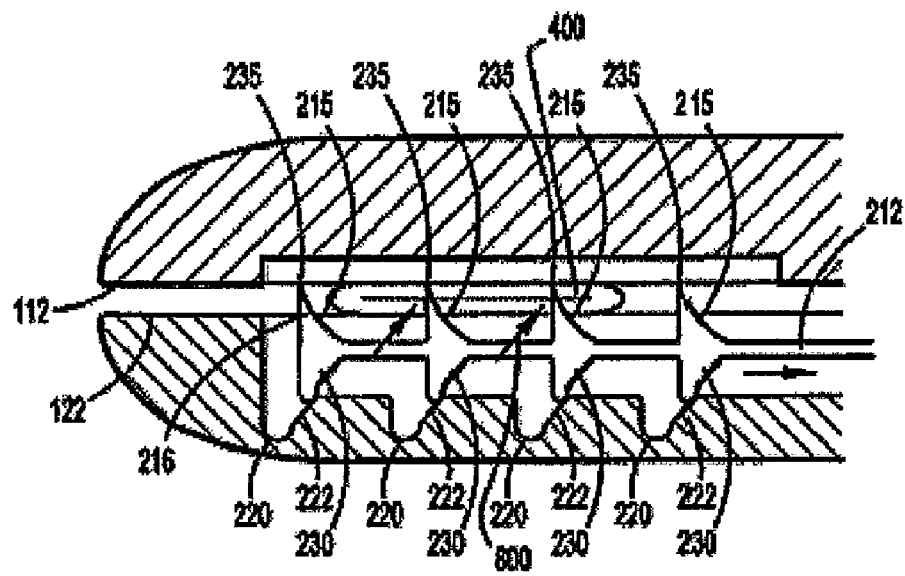
FIG. 8C is a greatly-enlarged schematic, side cross sectional view of the end effector assembly of FIG. 1A shown in a closed configuration with tissue therein during actuation.

FIG. 8B, shows jaw members 110 and 120 closing about tissue 400 in accordance with arrow 600'.

FIG. 8C, shows the blade 212 being actuated in a proximal direction. The proximal movement causes the plurality of flanges 230 to rub against the corresponding plurality of troughs 220, which results in cutting point 235 puncturing tissue 400. Arrow 800 shows the direction and angle of cutting point 235 being substantially equal to the incline of proximal wall 222.

Figure 8D:
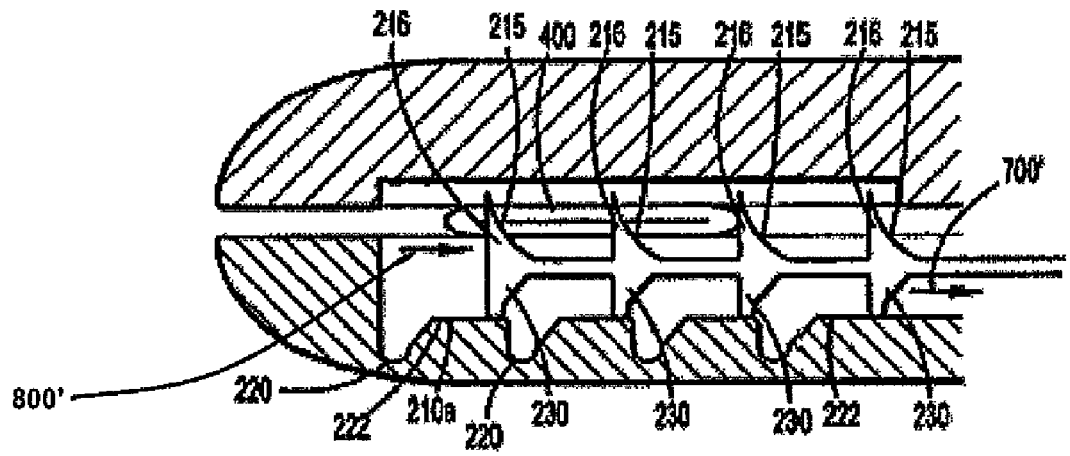
FIG. 8D is a greatly-enlarged schematic, side cross sectional view of the end effector assembly of FIG. 1A shown in a closed configuration with tissue therein during actuation.

Referring now to FIG. 8D, the blade direction is shown by arrow 700' as being actuated in a proximal direction. The proximal movement causes flange 230 to rub against blade channel 210a, which results in cutting edge 215 cutting across tissue 400. Arrow 800' shows the direction of cutting teeth 216 being substantially equal to wall 222 above trough 220.

From the foregoing and with reference to the various figure drawings, those skilled in the art will appreciate that certain modifications can also be made to the present disclosure without departing from the scope of the same. For example, although the proximal motion of the cutting path has been described, it is contemplated the troughs may be reversed so that the distal wall of trough 220 may be configured as a ramp with curvature or without curvature. Accordingly, distal actuation of the blade may be incorporated within blade channel depending upon a particular purpose and/or to facilitate manipulation by a user. Here, a user could push the blade through tissue instead of pulling it by proximal activation as described herein.

What is claimed is:

1. An electrosurgical forceps for sealing tissue, comprising:
    a pair of jaw members being movable from a first position in spaced relation relative to one another to at least one subsequent position wherein the jaw members cooperate to grasp tissue therebetween;
    each of the jaw members including an electrically conductive sealing plate adapted to connect to an energy source and configured to communicate energy through tissue held therebetween; and
    at least one of the jaw members having a blade channel defined therein configured for sliding redemption of a surgical blade assembly, the blade channel including a proximal end, a distal end and a plurality of troughs positioned therebetween, wherein the blade assembly includes:
        a blade body having a plurality of cutting elements extending therealong, each of said cutting elements including a cutting edge and a flange opposite the cutting edge, said blade body being selectively movable from a first position wherein said cutting edges of said cutting elements are recessed within said blade channel such that said cutting edges are positioned below the electrically conductive sealing plate and said flanges rest within corresponding troughs to at least one second position wherein said cutting edges are positioned above said electrically conductive sealing plate and into tissue grasped between the jaw members.

2. An electrosurgical forceps according to claim 1, wherein at least one of said troughs include an inclined surface such that movement of said blade body causes said flange to ride along said inclined surface to move said blade body towards the second position.

3. An electrosurgical forceps according to claim 1, wherein at least one of said troughs is dimensioned such that movement of said blade body causes said flange to move said cutting edge in at least one predetermined direction.

4. An electrosurgical forceps according to claim 1, wherein at least one of said troughs includes a bottom surface and a corresponding flange of said cutting element is dimensioned to include a surface which matingly engages said bottom surface of said trough.

5. An electrosurgical forceps according to claim 1, wherein at least one of said troughs includes a first surface and a second surface, said first surface being dimensioned to move said flange in a first direction upon movement of the blade body relative to the blade channel and a second surface dimensioned to move said flange in a second direction upon movement of the blade body relative to the blade channel.

6. An electrosurgical forceps according to claim 1, wherein the flanges and their respective troughs are in sliding communication so that movement of the flanges in a linear direction along a length of the blade channel directs the cutting elements to move in at least one direction relative to the blade channel.

7. An electrosurgical forceps according to claim 1, wherein the cutting edge of the cutting element is substantially curved.

8. An electrosurgical forceps according to claim 1, wherein the cutting edge of the cutting element is substantially straight.

9. A method of cutting tissue comprising:
    providing an electrosurgical forceps for sealing tissue, comprising:
        a pair of jaw members being movable from a first position in spaced relation relative to one another to at least one subsequent position wherein the jaw members cooperate to grasp tissue therebetween;
        each of the jaw members including an electrically conductive sealing plate adapted to connect to an energy source and configured to communicate energy through tissue held therebetween; and
        at least one of the jaw members having a blade channel defined therein configured for sliding reception of a surgical blade assembly, the blade channel including a proximal end, a distal end and a plurality of troughs positioned therebetween, the blade assembly includes:
            a blade body having a longitudinal axis defined therethrough and having a plurality of cutting elements extending therealong, each of said cutting elements including a cutting edge and an opposing flange, said blade body being selectively movable from a first position wherein said cutting edges of said cutting elements are entirely recessed within said blade channel and said opposing flanges rest within corresponding troughs to at least one second position wherein said cutting edges extend beyond said blade channel and into tissue grasped between the jaw members;
    positioning the jaw members about tissue; and
    moving the blade body in at least one direction such that at least one of said flanges rides along a respective trough and extends said cutting edges of said cutting elements into and through said tissue.

10. A method according to claim 9, wherein dimensions of the flange and the trough move the cutting edges of the cutting elements in a substantially angled manner relative to the blade channel.

11. A method according to claim 9, wherein the dimensions of the flange and the trough move the cutting edges of the cutting elements in a first direction relative to the blade channel to perforate the tissue and then in a second direction to cut the tissue.

* * * * *